United States Patent [19]
Suskind et al.

[11] Patent Number: 5,849,816
[45] Date of Patent: *Dec. 15, 1998

[54] METHOD OF MAKING HIGH PERFORMANCE SUPERABSORBENT MATERIAL

[75] Inventors: Stuart P. Suskind, Wayne, Pa.; Leonard Pearlstein, 1441 Waverly Ave., Gladwyne, Pa. 19035

[73] Assignee: Leonard Pearlstein, Gladwyne, Pa.

[*] Notice: The term of this patent shall not extend beyond the expiration date of Pat. No. 5,539,019.

[21] Appl. No.: 593,332

[22] Filed: Jan. 31, 1996

Related U.S. Application Data

[63] Continuation-in-part of Ser. No. 460,623, Jun. 2, 1995, abandoned, which is a continuation-in-part of Ser. No. 283,559, Aug. 1, 1994, Pat. No. 5,549,590.

[51] Int. Cl.$^6$ .............................. C08L 33/02; C08K 3/34; C08K 3/00; B32B 27/02

[52] U.S. Cl. ....................... 523/201; 523/202; 523/204; 428/407

[58] Field of Search ................................... 523/200–205, 523/209; 428/407

[56] References Cited

U.S. PATENT DOCUMENTS

| | | |
|---|---|---|
| Re. 32,649 | 4/1988 | Brandt et al. . |
| Re. 33,839 | 3/1992 | Chmelir et al. . |
| 3,544,500 | 12/1970 | Osmond et al. . |
| 3,932,322 | 1/1976 | Duchane . |
| 3,935,363 | 1/1976 | Burkholder et al. . |
| 3,992,558 | 11/1976 | Smith-Johannsen et al. . |
| 4,058,124 | 11/1977 | Yen et al. . |
| 4,081,402 | 3/1978 | Levy et al. . |
| 4,093,776 | 6/1978 | Aoki et al. . |
| 4,135,943 | 1/1979 | Morishita et al. . |
| 4,217,901 | 8/1980 | Bradstreet et al. . |
| 4,239,043 | 12/1980 | Gellert . |
| 4,242,251 | 12/1980 | Aishima et al. . |
| 4,245,005 | 1/1981 | Regnier et al. . |
| 4,286,082 | 8/1981 | Tsubakimoto et al. . |

(List continued on next page.)

FOREIGN PATENT DOCUMENTS

| | | |
|---|---|---|
| 0107500 | 2/1983 | European Pat. Off. . |
| 0388120 | 9/1990 | European Pat. Off. . |
| 0401806 | 7/1991 | European Pat. Off. . |
| 0 457 660 | 11/1991 | European Pat. Off. . |
| 0621041 | 10/1994 | European Pat. Off. . |
| 0629411 | 12/1994 | European Pat. Off. . |
| 51-1125683 | 11/1976 | Japan . |
| 56-131683 | 10/1981 | Japan . |
| 59-038271 | 3/1984 | Japan . |
| 62-210054 | 9/1987 | Japan . |
| 63-210109 | 8/1988 | Japan . |
| 1-56785 | 3/1989 | Japan . |
| 1-141938 | 6/1989 | Japan . |
| 2-2241541 | 9/1990 | Japan . |
| 61-058657 | 1/1991 | Japan . |
| 4-011948 | 1/1992 | Japan . |
| 2231573 | 11/1990 | United Kingdom . |
| WO86/04910 | 8/1986 | WIPO . |
| WO90/08789 | 8/1990 | WIPO . |
| WO 91/15177 | 10/1991 | WIPO . |
| WO93/17066 | 9/1993 | WIPO . |
| WO 93/24153 | 12/1993 | WIPO . |

OTHER PUBLICATIONS

Chemical Abstracts, vol. 88, p. 39, Nos. 88:51682y and 88:51683z, 1978.

*Primary Examiner*—John G. Weiss
*Assistant Examiner*—Dennis Ruhl
*Attorney, Agent, or Firm*—Finnegan, Henderson, Farabow, Garrett & Dunner, L.L.P.

[57] ABSTRACT

A high performance absorbent particulate composition and a method of preparation in which a non-colloidal solid filler core is substantially encapsulated within a layer of hydrogel forming polymer is disclosed. Also disclosed are absorbent devices using the high performance absorbent particulate composition and methods of making these devices.

28 Claims, 3 Drawing Sheets

U.S. PATENT DOCUMENTS

| | | |
|---|---|---|
| 4,292,987 | 10/1981 | Parks . |
| 4,324,247 | 4/1982 | Aziz . |
| 4,333,464 | 6/1982 | Nakano . |
| 4,340,706 | 7/1982 | Obayashi et al. . |
| 4,342,314 | 8/1982 | Radel et al. . |
| 4,392,908 | 7/1983 | Dehnel . |
| 4,418,163 | 11/1983 | Murakami et al. . |
| 4,446,261 | 5/1984 | Yamasaki et al. . |
| 4,454,055 | 6/1984 | Richman et al. . |
| 4,467,012 | 8/1984 | Pedersen et al. . |
| 4,474,852 | 10/1984 | Craig . |
| 4,500,670 | 2/1985 | McKinley et al. . |
| 4,507,438 | 3/1985 | Obayashi et al. . |
| 4,535,098 | 8/1985 | Evani et al. . |
| 4,587,308 | 5/1986 | Makita et al. . |
| 4,634,440 | 1/1987 | Widlund et al. . |
| 4,646,730 | 3/1987 | Schonfeld et al. . |
| 4,655,757 | 4/1987 | McFarland et al. . |
| 4,666,983 | 5/1987 | Tsubakimoto et al. . |
| 4,683,274 | 7/1987 | Nakamura et al. . |
| 4,732,968 | 3/1988 | Obayashi et al. . |
| 4,735,987 | 4/1988 | Morita et al. . |
| 4,742,086 | 5/1988 | Masamizu et al. . |
| 4,771,086 | 9/1988 | Martin . |
| 4,777,232 | 10/1988 | Heidel . |
| 4,783,510 | 11/1988 | Saotome . |
| 4,795,762 | 1/1989 | Diamantoglou et al. . |
| 4,800,103 | 1/1989 | Jeffs . |
| 4,880,870 | 11/1989 | Zimmermann et al. . |
| 4,888,238 | 12/1989 | Katz et al. . |
| 4,914,066 | 4/1990 | Woodrum . |
| 4,944,735 | 7/1990 | Mokry . |
| 4,950,264 | 8/1990 | Osborn, III . |
| 4,952,550 | 8/1990 | Wallach et al. . |
| 4,977,192 | 12/1990 | Martineu et al. . |
| 4,992,326 | 2/1991 | Dabi . |
| 5,019,063 | 5/1991 | Marsan et al. . |
| 5,032,425 | 7/1991 | Livsey et al. . |
| 5,061,259 | 10/1991 | Goldman et al. . |
| 5,074,856 | 12/1991 | Coe et al. . |
| 5,078,909 | 1/1992 | Shigeta et al. . |
| 5,079,004 | 1/1992 | Blank et al. . |
| 5,082,723 | 1/1992 | Gross et al. . |
| 5,118,719 | 6/1992 | Lind . |
| 5,145,906 | 9/1992 | Chambers et al. . |
| 5,147,343 | 9/1992 | Kellenberger . |
| 5,147,921 | 9/1992 | Mallo . |
| 5,154,713 | 10/1992 | Lind . |
| 5,180,622 | 1/1993 | Berg et al. . |
| 5,180,798 | 1/1993 | Nakamura et al. . |
| 5,188,899 | 2/1993 | Matsumoto et al. . |
| 5,196,456 | 3/1993 | Nguyen et al. . |
| 5,196,473 | 3/1993 | Valenta et al. . |
| 5,230,958 | 7/1993 | Dabi . |
| 5,250,642 | 10/1993 | Ahmed et al. . |
| 5,258,448 | 11/1993 | Mallo et al. . |
| 5,264,471 | 11/1993 | Chmelir . |
| 5,286,770 | 2/1994 | Bastioli et al. . |
| 5,300,358 | 4/1994 | Evers . |
| 5,539,019 | 7/1996 | Suskind et al. ............ 523/202 |

METHOD OF MAKING HIGH PERFORMANCE SUPERABSORBENT MATERIAL

This application is a continuation-in-part of U.S. patent application Ser. No. 08/460,623, filed Jun. 2, 1995, now abandoned which is a continuation-in-part of U.S. patent application Ser. No. 08/283,559, filed Aug. 1, 1994, now Pat. No. 5,549,590 the contents of which are relied upon and are incorporated herein by reference.

BACKGROUND OF THE INVENTION

The present invention relates to absorbent particles and an improved method of making such particles, for eventual use in absorbent articles, such as disposable diapers and sanitary pads.

Generally, absorbent articles are designed to have at least three distinct layers:

(1) a liquid pervious topsheet of bonded fibers usually referred to as a non-woven or an apertured film;
(2) an absorbent core containing mainly hydrophilic fibers such as a loose mat of pulp fibers usually referred to as "fluff" often contributing as much as 90% of the overall thickness of the article; and
(3) a liquid barrier outer film which is usually a polyolefin at a thickness of about 0.5–1.5 mils.

Fluids passing through the topsheet are distributed by the pulp fibers and are held within the interstices of the pulp web. Increases in pulp content generally lead to increases in the absorbent capacity of these devices. In light of the relatively low cost of pulp, absorbent articles are often designed with thick, bulky cores to provide high capacity in the absorbent article. The inherent disadvantages of such bulkiness are lack of comfort, visibility through clothing, and the inability of the article to conform to the shape of the body leading to unpredictable shifting and even fluid leakage. Importantly, these bulky items require precious storage space in distribution and in ultimate usage.

The development of superabsorbent polymers (SAP) which absorb at least 3–4 times as much fluid as pulp, has led to the successful design of much thinner products in which a substantial portion of the fluff has been replaced by SAP granules. While the consumer has accepted and even preferred these thinner articles, certain performance attributes are still not satisfactory and improvements are sought. For example, leakage is still one of the most important and the most critical deficiency remaining in disposable diaper design.

One approach taken to solve this problem has been to incorporate yet more SAP into the product. It is not uncommon in ultra-thin diapers to use as much as 6–15 grams of SAP granules per diaper accounting for up to 60% by weight of the absorbent core in order to achieve significant reductions in bulk or thickness and still provide needed performance.

SAP, generally, are polymeric materials containing water-insoluble long chain molecules with a low degree of cross-linking which are capable of forming hydrogel networks. In the presence of water or aqueous solutions such as body fluid, these hydrogel networks swell into a soft, resilient "jelly-like" material. When the swelling fluid is 0.9% saline, urine, or synthetic urine, these polymers may ultimately swell up to about 25–40 times their original weight. On the other hand, pulp fibers have a capacity to swell by a factor of only about 7–10 times by comparison.

The SAP materials are typically produced as granules which may then be mixed with pulp fibers during the formation of the absorbent core. Thus, with such highly absorbent granular material, it becomes possible to design and produce absorbent articles with roughly ½ to ⅓ of the bulkiness of the 100% pulp core. Reduction in volume of this nature is the subject of numerous U.S. Patents including for example, U.S. Pat. Nos. 4,950,264 (Osborn); 4,467,012 (Pederson); and 4,217,901 (Bradstreet), all incorporated in their entirety by reference herein.

There is unfortunately a disadvantage associated with this improvement. For while SAP is about three-fold more absorbent than pulp, its cost may be about four-fold higher. It is not surprising, therefore, that considerable effort has been dedicated toward maximizing or optimizing the cost effectiveness of the superabsorbent. These efforts are the subject of numerous U.S. patents. For example, particle size, modules, degree of neutralization, and residual monomers, are discussed in U.S. Pat. Nos. Re. 32,649 (Brandt) and 5,061,259 (Goldman et al.), both incorporated in their entirety by reference herein.

Furthermore, technical contributions were reported at the Advances in Superabsorbent Polymers Symposium, Fall Meeting 1993 of the American Chemical Society, as published in the Proceedings of the Division of Polymeric Materials: Science and Engineering (Masuda, p. 464; Nagorski, p. 560), incorporated herein by reference.

Prior to the trend toward thinner diapers, SAP was designed initially for maximum capacity and later with increased cross-linking for improved gel stability and absorbency under a load. With the trend toward thinner construction, the speed of liquid acquisition and distribution are also important properties. Accordingly, while SAP particles usually swell to capacity after about one hour exposure to fluid, the uptake rate during the first ten to twenty minutes is now considered critical.

It has been recognized that the rate of absorption could be increased through higher cross-link density of the SAP since the resulting increase in gel strength helps to maintain particle identity during swelling thus reducing particle coalescence. The effect of the latter phenomenon known as "gel blocking" is to block the open spaces in the web, causing a decrease in the rate of absorption. The undesirable drawback with increased cross-linking is the associated reduction in fluid capacity. In U.S. Pat. Nos. 4,587,308 (Makita) and 4,507,438 (Obayashi) (both incorporated in their entirety by reference herein), particles are subjected to cross-linking on the particle surface thereby increasing surface gel strength without compromising the swell capacity within the particle.

In U.S. Pat. No. 3,932,322 (Duchane) (incorporated in its entirety by reference herein), the tendency for particle agglomeration is reduced by admixing a small amount of very fine inorganic oxide particles which tend to coat the SAP particles.

The problem of reduced rate due to blocking of fluid is also addressed in U.S. Pat. No. 5,147,343 (Kellenberger) (incorporated in its entirety by reference herein), wherein the size of the superabsorbent particle is selected to be larger than the pore size of the absorbent core (i.e., at least about 100 microns). This design feature is claimed to provide improved absorbency under a load or under the weight of the user's body.

The importance of particle size is further taught in U.S. Pat. No. 5,180,622 (Berg et al.) (incorporated in its entirety by reference herein). This patent, more specifically, discloses that surface area of the particles controls the rate of fluid uptake. Since small particles have the more favorable ratio of surface area to mass, theory would predict a higher absorption rate with relatively small particles, i.e., about 50

μm. In fact, due to ease of packing, particles this size tend to form a mass of coagulated gel and fluid and flow is impeded by their "gel blocking." In the Berg et al. patent, the trade-off between fluid uptake and gel coagulation is resolved through a process which chemically links small particles into a larger cluster or agglomerate. These new particles have significantly higher swell rates than the precursor particles based on the high surface to mass ratio; however, this benefit is offset to some degree by increased processing cost. Furthermore, it is known that the efficiency of SAP in absorbing fluid content decreases as SAP content increases from, for example, about 20% by weight to about 60% by weight.

Another approach to solving the trade-off problem is to simply use larger quantities of larger particles; the drawback here is that increased volumes of SAP create additional expense for the manufacturer.

SUMMARY OF INVENTION

In light of the high cost of superabsorbent polymers and the need to find efficient and improved ways to utilize their properties, it is desirable to provide granular superabsorbent polymers in a novel form which offers important improvements and advantages over previous compositions.

Improvements in cost and performance of disposable absorbent devices such as, for example, disposable baby diapers, garments and pads designed to aid in fluid control for adult incontinence, and sanitary napkins for feminine hygiene are needed where fluid control properties are achieved through selection of absorbent fibers such as pulp and superabsorbent polymers typically in the form of granules.

It is especially desirable to increase the ratio of superabsorbent polymer to absorbent fibers to levels as high as 50% and even 60% by weight superabsorbent to provide thin, compact, and low cost devices that are comfortable to the wearer, highly effective in absorbing fluids, and reasonable in cost. Since the cost of superabsorbent polymer is relatively high in comparison to pulp, a successful design of the absorbent products which provides a high level of value to the end-user will necessarily make the most effective use of the superabsorbent employed.

Accordingly, to achieve these and other advantages and in accordance with the purpose of the present invention, as embodied and broadly described herein, the present invention relates to a plurality of non-agglomerated and discrete absorbent particles having a non-colloidal, water-resistant solid core and a hydrogel forming polymer substantially encapsulating the solid core.

An additional feature of the present invention is a method of making these absorbent particles having a particle size of $D_{AP}$. In this method, non-colloidal water resistant solid particles having a particle size $D_{CP}$ are individually suspended in a water immiscible solvent in the presence of a surface active agent. An ethylenically unsaturated monomer capable of polymerizing into a hydrogel forming polymer is suspended in the water immiscible solvent along with an initiator. The monomer is then polymerized such that the non-colloidal, water resistant solid particles are individually and substantially encapsulated with a polymer coating thickness T by the hydrogel forming polymer to form an absorbent particle having a particle size $D_{AP}$. In this method of making the plurality of absorbent particles, $D_{AP}$ has a value in the range of about 30 microns to about 2000 microns, $D_{CP}$ has a value in the range of about 10 microns to about 150 microns, and T has a value in the range of about 10 microns to about 995 microns.

An additional feature of the present invention is an absorbent device having fibers and a plurality of absorbent particles of the present invention. The absorbent device can be, for example, a disposable diaper, a female sanitary napkin, a urinary incontinence pad for adults, a bed pad, a pad for absorbing fluids from food, or a bandage.

The present invention also relates to a process for manufacturing absorbent devices of the present invention wherein absorbent particles of the present invention are interdispersed into an absorbent core comprising fibers. This absorbent core containing the absorbent particles is then interposed between a liquid pervious topsheet and a liquid impervious backsheet. The edges of the topsheet and backsheet are then sealed together by techniques well known in the art to create a liquid barrier around the entire circumference of the absorbent device.

The present invention further relates to a process for making absorbent particles. In this process, an aqueous solution containing an ethylenically unsaturated monomer capable of polymerizing into a hydrogel forming polymer and an initiator is first suspended in a water immiscible solvent in the presence of a surface active agent. This aqueous solution suspended in the water immiscible solvent is then heated to initiate polymerization. At a predetermined conversion level of monomer to polymer, water resistant solid particles, such as sand, are then co-suspended in the aqueous solution containing the water immiscible solvent. During polymerization, the water resistant solid particles are individually and substantially encapsulated by the hydrogel forming polymer to form an absorbent particle. After the polymerization step, the absorbent particles can be crosslinked, isolated, and then dried.

Additional features and advantages of the present invention will be set forth in part in the description which follows, and in part will be apparent from the description, or may be learned by practice of the present invention. The objectives and advantages of the invention will be realized and attained by means of the elements, combinations, composition, and process particularly pointed out in the written description and appended claims, as well as the appended drawings and photographs.

To achieve additional objectives in accordance with the purpose of the present invention as embodied and broadly described herein, the present invention relates to an absorbent device comprising a combination of hydrophilic and/or hydrophobic fibers and a plurality of superabsorbent polymer particles wherein said particles comprise a non-colloidal, non-water-swellable solid core, which is substantially encapsulated by a hydrogel forming polymer.

The present invention further relates to a process for making these absorbent particles which includes the steps of individually suspending non-colloidal solid particles in a water immiscible solvent in the presence of a surface active agent and then suspending in the water immiscible solvent, an aqueous solution of an ethylenically unsaturated monomer capable of polymerization into a hydrogel forming material, and an initiator. In the next step of the process, the monomer is polymerized such that the non-colloidal solid particles are individually and substantially encapsulated by the hydrogel forming polymer to form absorbent particles. After this polymerization step, the formed absorbent particles are separated from the solvent and dried.

By providing absorbent particles having a non-colloidal water resistant solid core substantially encapsulated by a hydrogel forming polymer, the polymer is readily available and is so structured physically to provide a high ratio of surface area to mass, a high rate of fluid absorption, a high level of gel stability, and a high absorbent capacity under load, thereby providing improved fluid absorbing efficiency when used in diapers and other absorbent composites, articles, and devices.

It is to be understood that both the foregoing general description and the following detailed description are exemplary and explanatory and are intended to provide further explanation of the present invention as claimed.

The accompanying drawings and photographs which are included to provide a further understanding of the present invention and are incorporated in and constitute a part of this specification, illustrate various embodiments of the present invention and together with the description serve to explain the principles of the present invention.

DETAILED DESCRIPTION

Figure 1:
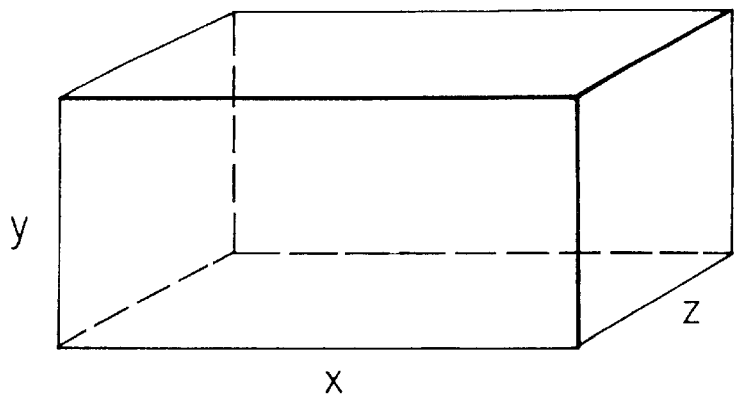
FIG. 1 is a diagrammatic representation of an absorbent core in accordance with the present invention.

Reference will now be made in detail to the present invention and various embodiments thereof, examples of which are illustrated in the accompanying drawings.

With respect to the absorbent particle(s) of the present invention, the particle comprises a non-colloidal, water-resistant solid core substantially encapsulated by a hydrogel forming polymer.

The non-colloidal water resistant solid core serves, in part, as a filler in order to provide a low cost core which is eventually substantially encapsulated by a hydrogel forming polymer. Generally, the size of the solid core, as measured by standard mesh screens, can range from about 10 microns to about 1500 microns, preferably from about 25 microns to about 1000 microns, and more preferably from about 100 microns to about 600 microns. The core can be any shape, e.g., spherical, oval, polyhedral, irregular, and non-spherical.

The weight ratio of solid core to hydrogel forming polymer in the absorbent particle of the present invention is at least about 1:4 and as high as about 9:1, and preferably from about 2:3 to about 2:1.

Typically, each particle of solid core is individually, discretely, and completely contained (i.e., encapsulated) by the hydrogel forming polymer. Occasionally, two or more solid core particles are contained in a single discrete absorbent particle. In some instances, a particle of solid core may not be completely encapsulated, but in most instances, and preferably, the particle of solid core is substantially (e.g., at least about 80% of the surface area of the core is covered with hydrogel forming polymer, preferably at least about 90%, and more preferably at least about 95%), if not completely, encapsulated by the hydrogel forming polymer.

It is to be understood that the term "water resistant" is herein used for purposes of the present invention to mean that the non-colloidal solid core is insoluble in water and aqueous solutions and non-swellable (at temperatures below about 90° F.) in water and aqueous solutions yet it is wettable with water and aqueous solutions.

Although there is no intention to limit the present invention to any particular non-colloidal, water resistant solid core material, the solid core material can be, for example, one or more materials selected from any of the following groups as long as the core can be encapsulated by the hydrogel forming polymer:

a) water insoluble inorganic minerals including, but not limited to, silicon dioxide, titanium dioxide, magnesium oxide, antimony oxide; clay, talc, wollastonite; synthetic amorphous silica; calcium carbonate; hollow mineral spheres, and the like, including the minerals described in Van Nostrand's Scientific Encyclopedia (1989), Seventh Edition, pages 1864–65, incorporated herein by reference; and b) water insoluble organic materials in particulate or granulated form including but not limited to cereals and cereal components such as hull, bran, flour, germ, and meal; nut shells, wood flour, sawdust, cellulose, microcrystalline cellulose, starch, gelatin, and the like.

Various mixtures and combinations of the foregoing materials can also be used as core filler materials in accordance with the present invention.

With regard to the hydrogel forming polymer, certain preferred water insoluble polymeric compositions useful in the present invention are listed below. The polymers set forth below and containing acid groups can be, as an option, partially or completely neutralized with alkali metal bases either as the monomer or the polymer or both. While the list below contains many of the preferred polymers which may be used in accordance with the present invention, the present invention is not limited to just these polymers and generally polymers traditionally understood as SAP by those skilled in the art can also be used:

a) polyacrylic acid, polymethacrylic acid, polymaleic acid, copolymers thereof, and alkali metal and ammonium salts thereof;

b) graft copolymers of starch and acrylic acid, starch and saponified acrylonitrile, starch and saponified ethyl acrylate, and acrylate-vinyl acetate copolymers saponified;

c) polyvinyl alcohol, polyvinylpyrrolidone, polyvinyl alkylether, polyethylene oxide, polyacrylamide, and copolymers thereof;

d) copolymers of maleic anhydride and alkyl vinylethers; and e) saponified starch graft copolymers of acrylonitrile, acrylate esters, vinyl acetate, and starch graft copolymers of acrylic acid, methyacrylic acid, and maleic acid.

The above exemplary polymers can be used in their linear state, or optionally, cross-linked either during the polymerization or after the core is encapsulated. This cross-linking can be achieved by methods known to those skilled in the art, including the use of a cross-linking agent. This cross-linking can be initiated in the presence of radiation or a chemical free radical initiator.

Polyfunctional cross-linking agents useful in the present invention include epichlorohydrin and related halo epoxy compounds, diglycidyl ether compounds, diisocyanates, polyaldehydes, and polyfunctional amines and imines.

Polyfunctional ethylenically unsaturated cross-linking agents include N,N',-methylene bisacrylamide, trimethylolpropanetriacrylate, ethylene glycol bismethacrylate, polyethylene glycol bismethacrylate, and divinyl benzene. The use of additional polymer cross-linking agents to modify the properties of gel forming polymers is well known and described in U.S. Pat. No. 4,783,510 as well as by Yin, Y., Polyelectrolyte Gels, Chapter 6, American Chemical Society, 1992, both incorporated herein by reference.

Hydrogel forming polymers and methods of preparation are known in the art and these polymers can be used in the present invention including the polymers in which divalent cations are used as cross-linking agents as set forth in U.S. Pat. Nos. 4,507,438; 5,145,906; 5,196,456; 5,250,642; and 4,295,987, all of which are incorporated herein by reference.

The particles of the present invention generally conform to the shape of the core particle. For example, where the core material is silica, the resulting absorbent particle is irregular in shape having a combination of flat and rounded surfaces and having various degrees of sharp and rounded corners and edges.

In the present invention, average absorbent particle size and absorbent particle size distribution can be achieved by appropriate selection of the core particle size. Through knowledge of the specific gravity and weight ratio of both the core material and hydrogel forming polymer, the growth in size of the absorbent particle is predictable.

The core particles of the present invention are substantially encapsulated by the polymer in such a way that the increase in particle diameter is predictable and controllable. It has been an objective in the field of superabsorbent polymers to provide granules within a controlled and pre-determined particle size range. The present invention provides for the first time, a practical, low cost method for achieving this goal. This novel and new property of controlled particle size is represented by the following mathematical expression:

$$D_{AP} = D_{CP} + 2T$$

wherein $D_{AP}$ is the diameter of the absorbent particle containing an encapsulated core particle;

$D_{CP}$ is the diameter of the core particle; and

T is the thickness of the superabsorbent or hydrogel forming polymer coating which encapsulates the core particle.

Within the scope of the present invention, DAP has a value in the range of about 30 microns to about 2000 microns. $D_{CP}$ has a value in the range of about 10 microns to about 150 microns. T has a value in the range of about 10 microns to about 995 microns.

The physical structure of these new particles is new and unique and imparts the desirable properties achieved through the present invention. These include:

1. The absorbent particles are separate and individual and predictable in size by means of the present invention.
2. The great majority of absorbent particles contain one core particle. A minor quantity of absorbent particles contain zero or two core particles.
3. The core particle is centrally located within the absorbent particle.
4. The rigidity and water resistance of the core particle provide an absorbent particle which is high in modulus and gel strength, contributing favorably to the absorbency under load.
5. The particles provide a high ratio of surface area to volume.

For example, an increase of about 50% in the ratio of polymer surface area to polymer volume is realized when comparing a SAP spherical particle of 100% polymer to an example of the current invention in which a spherical particle contains a spherical silica core of 200 $\mu$ diameter with a 1:1 weight ratio of SAP to silica.

The coating thickness of the hydrogel polymer that encapsulates the filler core is preferably from about 2 $\mu$ to about 3000 $\mu$, more preferably about 50 $\mu$ to about 1000 $\mu$, and most preferably about 100 $\mu$ to about 300 $\mu$.

The preferred number average molecular weight of the hydrogel forming polymer that is un-crosslinked (e.g., linear) is at least about 250,000, more preferably from about 250,000 to about 450,000, more preferably from about 256,000 to about 400,000.

Preferably the outer surface of the hydrogel forming polymer that encapsulates the solid core is cross-linked. This cross-linked surface creates a high cross-linked density shell. Accordingly, the particles of the present invention preferably have this shell and the hydrogel forming polymer beneath this shell is either un-crosslinked or cross-linked to a lesser degree than the shell. This shell prevents gel-blocking (i.e., absorbent particles sticking together during swelling) and also provides increased absorbency under a load.

It is also possible to have a cross-linking gradient wherein the outermost regions (including the outer surface) is more crosslinked than the inner regions of the hydrogel forming polymer. Also, the entire hydrogel forming polymer can be crosslinked, wherein the crosslink density is substantially the same or varies throughout the polymer coating.

The high crosslinked density shell preferably comprises from about 1% to about 50% of the overall thickness of the hydrogel forming polymer encapsulating the filler core and more preferably from about 1% to about 20%.

The superabsorbent coating which encapsulates the core particle may be further characterized physically as:

a) strongly adherent to the core surface; moreover, in those instances where the solid core surface does not adequately attract and hold the polymer coating, it may be desirable to add coupling agents to the system either in the form of an added ingredient or a comonomer in the polymer backbone;

b) continuous and without significant cracks, holes, or breaks; and c) tough and abrasion resistant.

The attributes stated above are based upon examination of the absorbent particles of this invention under both optical and scanning electron microscopy. In addition, selected test procedures were conducted to measure the strength, cohesiveness, and adhesion of the coating to the core particle. These are described in Example 32.

While the process disclosed in the present invention may be conducted with surfactants (i.e., surface active agents) having an HLB factor of from about 2 to about 12; it is preferred that the range of HLB factor be from about 3 to about 7 and most preferably from about 3 to about 5. A preferred surface active agent or surfactant is SPAN 60® which is a fatty ester of a sugar. These types of surfactants are preferred because they minimize interparticle agglomeration. These findings are summarized in Table I, wherein particles of the present invention were prepared in the manner set forth in Example 1 except as noted in the Table and the particles contained 50 wt % silica and the polymer was not crosslinked. Optionally, surfactants that are fatty esters of a sugar that have been reacted with various levels of ethylene oxide can be used.

TABLE I

PARTICLE SIZE DEPENDENCE

| Starting | | | | Final Particle Size Analysis | | | | | |
| --- | --- | --- | --- | --- | --- | --- | --- | --- | --- |
| Sand Size (Mesh) | Surfactant Type | Surfactant Level | Net HLB | On 40 >420 | 40–60 420–250 | 60–100 250–150 | 100–200 150–75 | Thru 200 <75 | (mesh size) (particle size)* |
| 60–100 | Tween 81 Span 60 | 1.1 phr** 1.1 phr | 7.4 | 89.10 | 9.00 | 1.80 | 0.15 | 0.00 | |
| 100–140 | Tween 81 Span 60 | 1.1 phr 1.1 phr | 7.4 | 89.00 | 6.40 | 2.35 | 2.10 | 0.14 | |
| 100–140 | Tween 81 Span 60 | 2.75 phr 2.75 phr | 7.4 | 92.05 | 4.84 | 2.36 | 0.62 | 0.13 | |
| 60–100 | Tween 81 Span 60 | 2.75 phr 2.75 phr | 7.4 | 85.86 | 7.35 | 3.64 | 2.86 | 0.72 | |
| F-75 as is | Span 60 | 2.2 phr | 4.8 | 25.61 | 58.48 | 14.35 | 1.47 | 0.10 | |
| F-75 as is | Tween 81 | 2.2 phr | 10.0 | 50.94 | 37.77 | 8.19 | 3.07 | 0.04 | |

*in microns
**phr = parts per hundred resin (polymer)

Various stabilizers, dispersants, dyes, pigments, diluents and the like, as well as anti-microbial agents, odor absorbing compounds, and perfumes can also be part of the absorbent particle of the present invention.

With regard to methods of making the absorbent particle of the present invention, the following steps, e.g., can be used:

a) individually suspending non-colloidal water resistant solid particles in a water immiscible solvent in the presence of a surface active agent (i.e., surfactant);

b) suspending in the water immiscible solvent an aqueous solution of an ethylenically unsaturated monomer capable of polymerization into a hydrogel forming material and an initiator;

c) polymerizing the monomer such that the non-colloidal water resistant solid particles are individually and substantially encapsulated by the hydrogel forming polymer to form absorbent particles; and d) separating and drying the absorbent particles.

The hydrogel forming polymer can be crosslinked with polyfunctional cross-linking agents which are included in the aqueous solution in step (b) above Alternately, polyfunctional cross-linking agents can be added at the end of step (c) and prior to step (d) above. Cross-linking can occur by suspending the absorbent particles in step (d) in a solvent containing a polyfunctional cross-linking agent.

In one preferred aspect of the present invention, the absorbent particle is prepared from partially neutralized acrylate-acrylic acid mixture dissolved in water which is added, along with potassium persulfate (a free radical initiator) to a suspension of silica particles (Ottawa Foundry Sand, Grade F-75, U.S. Silica Company) and surfactant in an organic solvent such as cyclohexane. This particular grade of sand is supplied with a particle size range of from about 50 to about 600 microns with about 85% by weight of the particles in the range of from about 100 to about 200 microns. Neutralization may be carried out with alkali metal hydroxides (e.g., sodium) or ammonium hydroxides.

Sufficient agitation of the suspension, e.g., with a stirrer, is provided to allow the polymerization mixture to adsorb onto the exterior surface of the core material, e.g., silica particles. The mixture is heated at a temperature of from about 40° C. to about 60° C. for about 2–3 hours to polymerize the sodium acrylate-acrylic acid mixture.

After polymerization is complete, the suspended particles are separated (e.g., by decantation of the liquid components), dried, lightly ground and then classified, e.g., by using a sieve. Prior to separation, azeotropic distillation can be used to remove water from the polymer of the absorbent particles formed.

The average particle size of the resulting absorbent particles of the present invention are preferably in the range of from about 30 microns to about 2000 microns, preferably from about 100 microns to about 600 microns.

Typically from about 90 to about 95% weight yield of absorbent particles are in the size range of from about 100 to about 600 microns. Microscopic examination of the individual particles in the presence of water reveals sand particles substantially or fully encapsulated by hydrogel forming polymers.

Figure 5:
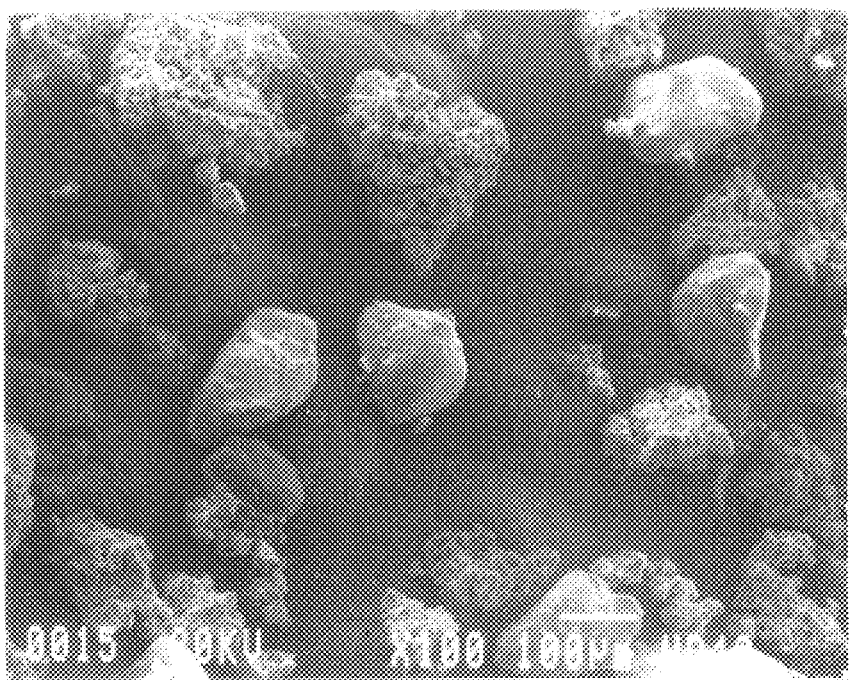
FIGS. 5 and 6 are microphotographs of absorbent particles of the present invention.
Figure 6:
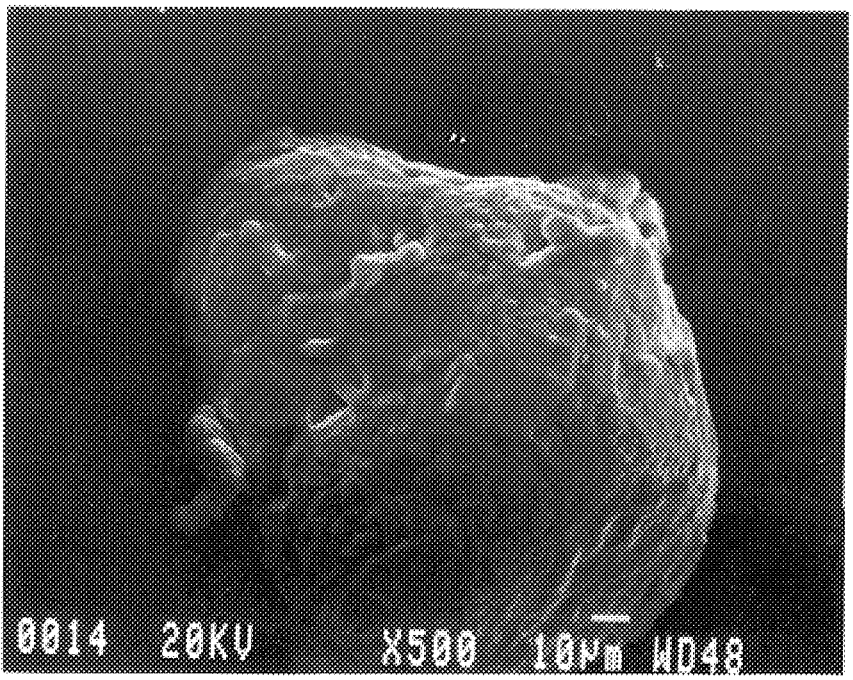

FIG. 5 is a scanning electron micrograph at 100× magnification of an absorbent particle of the present invention in which silica particles (Grade F-75 Ottawa Sand) are coated with a superabsorbent polymer by a method similar to Example 9. FIG. 6 is a 500× magnification of a particle in FIG. 5. The various non-porous surface textures from rough to smooth is believed to be due to the degree of particle coalescence as the polymerizing droplets are adsorbed on the inner core.

Depending upon the properties desired in the absorbent particles, the process may be modified by one skilled in the art without undue experimentation with respect to:

a) Particle size distribution of the filler core.
b) Weight ratio of filler core to polymer.
c) Composition of the polymer and crosslink density.
d) Nature and quantity of surfactant.
e) Degree of agitation.
f) Polymerization initiator.

Alternate methods for the preparation of the particles of the present invention are equally useful in that individualization of the non-colloidal solid core particle with subsequent coating by a hydrogel forming polymer is possible.

One alternative method for the preparation of the absorbent particles of the present invention which has certain advantages over the method described above is as follows. An aqueous solution of an ethylenically unsaturated monomer capable of polymerization into a hydrogel forming polymer is prepared and then suspended in a water immiscible solvent in the presense of a surface active agent. This overall mixture containing the aqueous solution and water immiscible solvent is then heated to initiate polymerization. Upon evidence of a polymerization reaction exotherm, water resistant solid core particles are co-suspended in water immiscible solvent. During polymerization, the water resistant solid core particles are individually and substantially encapsulated by the hydrogel forming polymer to form the absorbent particles. The resulting absorbent particles can then be cross-linked as described above in the previous method using a cross-linking agent; and the product can be isolated and dried in any manner such as the ways described above and in the examples.

In this method, besides the exemplary components described earlier, the preferred water resistant solid core particle is silicon dioxide or sand. The preferred ethylenically unsaturated monomer capable of polymerizing into a hydrogel forming polymer is partially neutralized acrylic acid. The preferred water immiscible solvent is heptane, cyclohexane and the like. The preferred initiator is potassium persulfate and the like and the preferred surface active agent is Tween 81/Span 60 and the like. However, those skilled in the art, after reading this application, will know of other suitable initiators and surface active agents.

This method has certain benefits compared to other methods. For instance, since the polymer suspension has increased in viscosity and tackiness prior to the addition of the water resistant solid core particles, the tendency for downward sedimentation of the water resistant solid core particles, especially when those particles are sand, is significantly reduced and the yield of desired absorbent particles is significantly improved.

Furthermore, in the process described prior to this process, on a large scale, the water resistant solid core particles can abrade the inner surface of a reaction vessel, leading to surface wear and ultimately to fatigue and failure of the reaction vessel. This improved process avoids the addition of the water resistant solid core particles until polymerization has begun. Thus, the water resistant solid core particles are rapidly surrounded by the more viscous polymer beginning to form. This results in less scraping or the complete avoidance of scraping of the inner surface of the reaction vessel.

The term "evidence of a polymerization reaction exotherm" in this context means an increase in temperature, e.g., to about 50° C. to about 70° C. of the polymer suspension. This exotherm is usually accompanied by a noticeable increase in viscosity of the suspension.

Further, other examples of methods to make the absorbent particles of the present invention include (1) a fluidized bed of particles in a vapor stream of monomer and initiator under polymerization conditions; and (2) mixing of the non-colloidal particle with monomer and initiator followed by atomization into a chamber which provides the necessary polymerization conditions. It is to be understood that the monomer and initiator are dissolved in a solvent such as water which is subsequently removed upon atomization.

Most superabsorbent polymers of commercial importance are prepared by the free radical induced polymerization of acrylic acid and salts thereof. In one process, an aqueous solution of partially neutralized monomer is polymerized in bulk followed by removal of water from the polymer mass and then grinding to the desired particle size. Particles with diameters below about 100 microns are generally considered to be an undesirable dust. In an alternate method, often referred to as "inverted suspension polymerization," the aqueous monomer solution, partially neutralized, is suspended as tiny droplets in a water immiscible solvent such as cyclohexane. After completion of the polymerization, water is removed and the polymer is recovered as specially shaped granules.

The above mentioned suspension process is described in U.S. Pat. Nos. 4,340,706 and 4,418,163, both of which are incorporated herein in their entirety by reference. Additionally, this preparation method is described in Chapter 2 of *Superabsorbent Polymers*, ACS Symposium Series 573 (1994), and is also incorporated herein in its entirety by reference.

In order to more clearly define the process of the present invention the following is presented as descriptive of the present invention, but does not necessarily represent a limitation of the present invention:

a) Before the addition of monomer, a quantity of non-colloidal water resistant particles is suspended in the water immiscible solvent with the aid of a surfactant.

b) An aqueous solution of monomer and a water soluble free radical initiator are co-suspended.

c) The polymerizing suspended droplets of monomer are adsorbed at the surface of the non-colloidal water resistant core particle and subsequently coalesce into a coating which substantially encapsulates the core particle.

d) The attraction for and adsorption on the core particle by the monomer droplets during the polymerization, preferably starts with the early stages of polymerization.

Generally, an absorbent device of the present invention will have a topsheet, a backsheet, and a core interposed between the topsheet and the backsheet. The backsheet will typically be a liquid impervious type of backsheet, and the topsheet will be a liquid pervious type topsheet of nonwoven material or a liquid pervious or impervious material having apertures. The absorbent core can be any design known to those in the art, including the absorbent core designs used in association with superabsorbent polymers such as in the patents described below, which are all incorporated in their entirety by reference herein.

The absorbent core used in an absorbent device will generally comprise fibers and a plurality of absorbent particles. These absorbent particles of the present invention can exist as a separate layer in the absorbent core or be interdispersed with the fibers in any manner known to those skilled in the art. Furthermore, the absorbent particles of the present invention can be substituted for a portion or all of the superabsorbent polymers described in the patents below. The fibers used in the absorbent device of the present invention will preferably be hydrophilic in nature and be in the form of a web. The web is preferably collected on a forming screen which is a process known to those skilled in the art. The absorbent device will generally contain absorbent particles of the present invention wherein the non-colloidal solid core comprises about 20% to about 70% by weight and the solid core has a particle size of from about 10 microns to about 1500 microns.

The absorbent cores used in the absorbent devices of the present invention, including fibers and the manner in which the absorbent core is used with SAP as described in U.S. Pat. Nos. 5,019,063; 5,300,358; 5,074,856; 4,944,735; 4,634,440; 4,342,314; 4,324,247; 4,217,901; 4,950,264; 5,147,343; 4,655,757; 5,061,259; and 5,286,770, can also be used with the absorbent particles of the present invention. A portion or all of the SAP referred to in these patents can be replaced with absorbent particles of the present invention.

Fibers used herein include, but are not limited to, mechanical pulp fibers, chemically-modified thermo-mechanical pulp fibers, cellulosic fibrous material, textile fibers, and the like. The absorbent can also be cellulose fluff, wood fluff, rayon, cotton, or meltblown polymers such as polyester, polypropylene, or coform.

The present invention also relates to a process for manufacturing absorbent devices of the present invention wherein absorbent particles of the present invention are interdispersed into an absorbent core comprising fibers.

This absorbent core containing the absorbent particles is then interposed between a liquid pervious topsheet and a liquid impervious backsheet. The edges of the topsheet and backsheet are then sealed together to create a liquid barrier around the entire circumference of the absorbent device.

The high performance superabsorbent particles of the present invention will be further clarified by the following examples, which are intended to be purely exemplary of the present invention.

EXAMPLES

The absorbent particles of the present invention were compared to a) a superabsorbent particle identified as FAVOR 800 which is commercially available from Stockhausen (Greensboro, N.C.). FAVOR 800 is believed to be a crosslinked polymer of partially neutralized acrylic acid; and b) a superabsorbent particle identified as ASAP 1000 which is commercially available from Chemdal (Palatine, Ill.). ASAP 1000 is also believed to be a crosslinked polymer of partially neutralized acrylic acid.

Example 1

A 1000 ml round bottom flask equipped with nitrogen inlet and outlet tubes, a reflux condenser, a Dean Stark trap, a mechanical stirrer, a thermometer, and an additional funnel were purged with nitrogen. 400 ml of cyclohexane, 548 mg of polyoxyethylene 5 sorbitan monooleate (available as TWEEN 81® from ICI Americas, Inc., Wilmington, Del.) and 540 mg of sorbitan monostearate (available as SPAN 60® from ICI Americas, Inc., Wilmington, Del.) were added to the flask and the internal temperature brought to 42° C. with stirring to disperse the sorbitan monostearate. After approximately 10 minutes, the above surfactants were solubilized and the contents of the flask were allowed to cool to room temperature (i.e., approximately 25° C.).

Concurrently with the foregoing, 40 ml acrylic acid and 10 ml deionized distilled water were stirred in a 250 ml round bottom flask under a nitrogen atmosphere with cooling provided by an ice bath. While cooling, 16.72 grams of sodium hydroxide dissolved in 50 ml deionized distilled water were added dropwise to the acrylic acid solution. 64 mg of potassium persulfate were then added to the partially neutralized acrylic acid solution. The mixture was stirred for approximately 10 minutes with cooling from the ice bath, then at ambient temperature to complete dissolution of the potassium persulfate and to form a sodium acrylate solution.

40 grams of Ottawa fine foundry sand (Grade F-75) with an AFS grain size of 75 were added to the cyclohexane/surfactant solution. The sodium acrylate solution was then added with vigorous stirring. The temperature of the reaction mixture was brought to 43° C. and held there for 2½ hours. Water was removed as an azeotrope with cyclohexane and the solid dried to give 92.6 grams of off-white granular product.

60 grams of the above product, previously screened through 30 mesh onto 60 mesh, were slurried in 84 ml of methanol. 8.2 ml of 6.8 mg/ml aqueous solution of ethylene glycol diglycidyl ether (56.2 mg) were added. The reaction mixture was heated and stirred at 50°–55° C. for 2 hours. The solvent was removed under reduced pressure and the solid was oven dried at 50° C. to give 62.3 grams of granular product of the present invention containing 44 wt. % silica.

Example 2

A 1000 ml round bottom flask equipped with nitrogen inlet and outlet tubes, a reflux condenser, a Dean Stark trap, a mechanical stirrer, a thermometer, and an addition funnel were purged with nitrogen. 400 ml cyclohexane, 548 mg of polyoxyethylene 5 sorbitan monooleate (available as TWEEN 81® from ICI Americas, Inc., Wilmington, Del.) and 540 mg of sorbitan monostearate (available as SPAN 60® from ICI Americas, Inc., Wilmington, Del.) were added to the flask and the internal temperature brought to 42° C. with stirring to disperse the sorbitan monostearate. After approximately 10 minutes, the contents of the flask were allowed to cool to room temperature.

Meanwhile, 40 ml of acrylic acid and 10 ml of de-ionized distilled water were stirred in a 250 ml round bottom flask under a nitrogen atmosphere with cooling provided by an ice bath. While cooling, 16.72 grams of sodium hydroxide dissolved in 50 ml de-ionized distilled water were added dropwise to the acrylic acid solution. 64 mg of potassium persulfate were added to the partially neutralized acrylic acid solution. The mixture was stirred for approximately 10 minutes with cooling from the ice bath, then at ambient temperature to complete dissolution of the potassium persulfate and to form a sodium acrylate solution.

62.58 grams of Ottawa fine foundry sand (Grade F-75) with an AFS grain size of 75 were added to the cyclohexane/surfactant solution. The sodium acrylate solution was then added with vigorous stirring. The temperature of the reaction mixture was brought to 43° C. and held there for 2½ hours. Water and cyclohexane azeotrope were distilled off and the solid was dried to give 114.3 grams of off white, granular product.

Example 3

Cross-Linked 36.5 grams, previously screened through 30 mesh onto 60 mesh, of the granular product of Example 2 was slurried in 35 ml of methanol. 4.0 ml of 6.8 mg/ml aqueous solution of ethylene glycol diglycidyl ether (27.44 mg) were added. The reaction mixture was heated and stirred at 50°–55° C. for 2 hours. The solvent was removed under reduced pressure and the solid was oven dried at 50° C. to give 37.3 grams of granular product with 55 wt. % of silica.

Example 4

Example 4 was prepared in a manner similar to the procedure of Example 1. The core material was Hubercarb grade Q20-60 (J-W Huber Corporation, St. Louis, Mo.) comprised typically of 96.5% calcium carbonate (2% by weight of the size of calcium carbonate was 1170 microns–1560 microns), 2.0% magnesium carbonate, and 1.2% silica. The particle size distribution was characterized as 90% (by weight) greater than 200 microns and 10% (by weight) greater than 900 microns with a median particle size of about 450 microns. The weight ratio was 45 parts filler to 55 parts polymer. Example 4 was prepared without cross-linking agents.

Example 5

Example 5 was a repeat of Example 1 except that after removal of 44 gm of water as an azeotrope, 15.4 mg of ethylene glycol diglycidyl ether in 5 ml of methanol were added and the reaction mixture held for 3 hours at 50° C. At the end of this time, the remainder of the water was removed by azeotropic distillation (10 ml). The granular product was recovered and dried in an oven at 65° C. for 4 hours.

Example 6

The objective of Example 6 was to increase the ratio of core filler to 72% by weight. Accordingly, a 1000 ml round bottom flask equipped with nitrogen inlet and outlet tubes, a reflux condenser, a Dean Stark trap, a mechanical stirrer, a thermometer, and an addition funnel were purged with nitrogen. 400 ml of cyclohexane, 548 mg of polyoxyethylene 5 sorbitan monooleate (available as TWEEN 81® from ICI Americas, Inc., Wilmington, Del.) and 540 mg of sorbitan monostearate (available as SPAN 60® from ICI Americas, Inc., Wilmington, Del.) were added to the flask and the internal temperature brought to 42° C. with stirring to disperse the sorbitan monostearate. After approximately 10 minutes, the contents of the flask were allowed to cool to room temperature.

Meanwhile, 20 ml acrylic acid and 10 ml deionized distilled water were stirred in a 250 ml round bottom flask under nitrogen atmosphere with cooling provided by an ice bath. While cooling, 8.36 grams of sodium hydroxide dissolved in 50 ml deionized distilled water were added dropwise to the acrylic acid solution. 33 mg potassium persulfate were added to the partially neutralized acrylic acid solution. The mixture was then stirred for approximately 10 minutes with cooling from the ice bath, then at ambient temperature to complete dissolution of the potassium persulfate and to form a sodium acrylate solution.

40 grams of Ottawa fine foundry sand (Grade F-75) with an AFS grain size of 75 were added to the cyclohexane/surfactant solution. The sodium acrylate solution was added with vigorous stirring. The temperature of the reaction mixture was brought to 55° C. and held there for 2½ hours. 41 ml of water was removed as an azeotrope with cyclohexane. At that point, 15.4 mg of ethylene glycol diglycidyl ether in 4.8 ml of methanol was added and the reaction mixture held for 3 hours at 50° C. The reaction mixture was cooled to room temperature overnight.

The reaction was heated and an additional 12 ml water removed by azeotropic distillation. The reaction mixture contains some granular solid and some solid adhering to the wall of the flask. The granular product was recovered and dried in an oven at 50° C. overnight. Deionized distilled water was added to the flask to swell off the solid adhering to the wall of the flask. The material was collected in a glass dish and allowed to dry. The solid exists as a mixture of small granules and larger ½-inch agglomerates.

Example 7

A 1000 ml round bottom flask equipped with nitrogen inlet and outlet tubes, a reflux condenser, a Dean Stark trap, a mechanical stirrer, a thermometer, and an addition funnel were purged with nitrogen. 400 ml of cyclohexane, 549 mg of polyoxyethylene 5 sorbitan monooleate (available as TWEEN 81® from ICI Americas, Inc., Wilmington, Del.), and 540 mg of sorbitan monostearate (available as SPAN 60® from ICI Americas, Inc., Wilmington, Del.) were added to the flask and the internal temperature brought to 42° C. with stirring to disperse the sorbitan monostearate. After approximately 10 minutes, the contents of the flask were allowed to cool to room temperature.

Meanwhile, 40 ml acrylic acid and 10 ml deionized distilled water were stirred in a 250 ml round bottom flask under nitrogen atmosphere with cooling provided by an ice bath. While cooling, 16.72 grams of sodium hydroxide dissolved in 50 ml deionized distilled water were added dropwise to the acrylic acid solution. 64 mg potassium persulfate were then added to the partially neutralized acrylic acid solution. The mixture was stirred for approximately 10 minutes with cooling from the ice bath, then at ambient temperature to complete dissolution of the potassium persulfate and to form a sodium acrylate solution. 27.5 gm of corn bran (Illinois Cereal Mills lot 99C-30) were added to the cyclohexane/surfactant solution. The sodium acrylate solution was then added with vigorous stirring. The temperature of the reaction mixture was brought to 55° C. and held there for 2½ hours. 43 gms of water were removed as an azeotrope with cyclohexane. A particulate phase and a fused phase were both present at the end of this time. The solid phase was removed (approximately 35 gm of material). At that point, 4.3 ml of solution containing 8.5 mg ethylene glycol diglycidyl ether were added to the reaction mixture and the reaction mixture held for 3 hours at 50° C. At the end of this time, the remainder of the water was removed by azeotropic distillation (10 ml). The granular product was recovered and dried in an oven at 65° C. for 4 hours.

Example 8

In Example 8, 4.0 gm of material prepared in the same manner as Example 6 were placed in a 50 ml flask along with 5.0 ml methanol plus 0.55 ml of a solution of ethylene glycol diglycidyl ether in methanol (10 mg/ml). The mixture was stirred at 55° C. for 2 hours and then separated and dried.

Example 9

A 1000 ml round bottom flask equipped with nitrogen inlet and outlet tubes, a reflux condenser, a Dean Stark trap, a mechanical stirrer, a thermometer, and an addition funnel were purged with nitrogen. 400 ml of cyclohexane, 550 mg of polyoxyethylene 5 sorbitan monooleate (available as TWEEN 81® from ICI Americas, Inc., Wilmington, Del.) and 540 mg of sorbitan monostearate (available as SPAN 60® from ICI Americas, Inc., Wilmington, Del.) were added to the flask and the internal temperature brought to 42° C. with stirring to disperse the sorbitan monostearate. After approximately 10 minutes, the contents of the flask were allowed to cool to room temperature.

At the same time, 40 ml acrylic acid and 10 ml deionized distilled water were stirred in a 250 ml round bottom flask under nitrogen atmosphere with cooling provided by an ice bath. While cooling, 16.72 grams of sodium hydroxide dissolved in 50 ml deionized distilled water were added dropwise to the acrylic acid solution. 64 mg potassium persulfate were added to the partial neutralized acrylic acid solution. The mixture was stirred for approximately 10 minutes with cooling from the ice bath, then at ambient temperature to complete dissolution of the potassium persulfate to form a sodium acrylate solution.

51.2 grams of Ottawa fine foundry sand (Grade F-75) with an AFS grain size of 75 were added to the cyclohexane/surfactant solution. The sodium acrylate solution was then added with vigorous stirring. The temperature of the reaction mixture was brought to 54° C. and held there for 2½ hours. Water was removed as an azeotrope with cyclohexane. 21 gms of water was removed as an azeotrope with cyclohexane. A particulate phase had formed at this point. At that point 3.4 ml of a methanol solution containing 10.2 mg ethylene glycol diglycidyl ether were added and the reaction mixture held for 2 hours at 50° C. Next, 23 ml of water was removed by azeotropic distillation. At that point another 3.4 ml of a methanol solution containing 10.2 mg ethylene glycol diglycidyl ether were added and the reaction mixture held for 2 more hours at 50° C. At the end of this time, the remainder of the water was removed by azeotropic distillation (14 ml). The granular product was recovered and dried in an oven at 65° C. for 4 hours. The total yield was 103.2 gm.

Example 10

A 1000 ml round bottom flask equipped with nitrogen inlet and outlet tubes, a reflux condenser, a Dean Stark trap, a mechanical stirrer, a thermometer, and an addition funnel were purged with nitrogen. 400 ml of cyclohexane, 550 mg of polyoxyethylene 5 sorbitan monooleate (available as TWEEN 81™ from ICI Americas, Inc., Wilmington, Del.) and 540 mg of sorbitan monostearate (available as SPAN 60® from ICI Americas, Inc., Wilmington, Del.) were added to the flask and the internal temperature brought to 42° C. with stirring to disperse the sorbitan monostearate. After approximately 10 minutes, the contents of the flask were allowed to cool to room temperature.

At the same time, 40 ml acrylic acid and 10 ml deionized distilled water were stirred in a 250 ml round bottom flask under nitrogen atmosphere and with cooling provided by an ice bath. While cooling, 16.72 grams of sodium hydroxide dissolved in 50 ml deionized distilled water were added dropwise to the acrylic acid solution. 64 mg potassium persulfate were added to the partially neutralized acrylic acid solution. The mixture was stirred for approximately 10 minutes with cooling from the ice bath, then stirred at ambient temperature to complete dissolution of the potassium persulfate and form a sodium acrylate solution. 30 gms of corn starch (Argo brand) were added to the cyclohexane/surfactant solution. The sodium acrylate solution was added with vigorous stirring. The temperature of the reaction mixture was brought to 55° C. and held there for 2½ hours. 42 gms of water were removed as an azeotrope with cyclohexane. A particulate phase has formed at this point. At that point 5.2 ml of a methanol solution containing 15.4 mg ethylene glycol diglycidyl ether were added and the reaction mixture held for 3 hours at 50° C. At the end of this time, the remainder of the water was removed by azeotropic distillation (16 ml). The granular product was recovered and dried in an oven at 65° C. for 4 hours. The total yield was 82.9 gm.

Example 11

In Example 11, 4.0 gm of material prepared in the same manner as Example 1 were placed in a 50 ml flask along with 5.0 ml methanol plus 0.55 ml of a solution of ethylene glycol diglycidyl ether in methanol (10 mg/ml). The mixture was stirred at 55° C. for 2 hours and then separated and dried.

Test Procedures

1. Swell Time to Gel

A sample is passed through U.S. 30 Screen and collected on U.S. 60 mesh. A test specimen, 0.25 gm, is placed in a 7.0 ml vial. Add 2.5 gm of 1.0% sodium chloride. Observe and record time for meniscus to disappear as sample gels.

2. Capacity

Place 0.3 gm on aluminum pan and weigh. Add 10 ml of 1% saline solution; cover with film and let stand for 1½ hours. Discard excess solution and weigh. Calculate:

$$\frac{(\text{wt. of absorbent particle} + \text{saline}) - \text{wt. of absorbent particle}}{\text{wt. of absorbent particle}}$$

3. Absorbency Under an External Load Purpose

Determine the amount of fluid absorbed by absorbent materials while placed under an external load as a function of time.

Conditions

A 0.016 gram sample of absorbent material is placed on a 20.28 cm$^2$ area, and a pressure of 21,000 dynes/cm$^2$ (approximately 0.3 lb/in$^2$) is applied.

Equipment

Electronic Balance (range: minimum of 200 g; accuracy: at least 0.001 g)

2.54 cm (1 inch) inner diameter (I.D.) cylinder (material: Plexiglass®) with a stainless steel screen (mesh: 100) fused to the cylinder bottom.

2.5273 cm (0.995 inch) piston (material: Plexiglass®) weighing 4.4 g.

100 g weight (balance calibration weight).

Timer

Controlled Atmosphere: Temperature 23° C (73.4° F.) Relative Humidity 50%

Procedure

1. Prepare 1 kg of 0.9% (w/w) NaCl solution or synthetic urine.
2. Screen absorbent material to a 30/60 cut and place the 30/60 cut of material in sealed storage containers to maintain constant product conditions.
3. Place 0.160 g of absorbent material onto pre-tared weighing paper. Record the actual absorbent material weight, $\underline{W}_p$, on a record sheet.
4. Slowly add the absorbent material into the cylinder with the screened bottom.
5. Gently tap the cylinder until the material is evenly distributed on the mesh. If absorbent material is on cylinder wall, the test is re-run.
6. Place piston into cylinder.
7. Place 100 g weight on piston.
8. Weigh the combined cylinder, piston and test material. Record this weight, $\underline{W}_c$, on the record sheet.
9. Pour thin layer of solution into pan.
10. Place filter paper into pan and allow the solution to saturate the filter paper.
11. Set timer for predetermined time interval (1 or 5 minutes) or a maximum time (i.e. 60 minutes). (Measurements conducted at various time intervals are used to calculate and develop an absorption curve for the absorbent material.)
12. Place the combined cylinder on the saturated filter paper and simultaneously start the timer.
13. Upon expiration of time, remove the combined cylinder and blot on paper toweling.
14. Weigh the combined cylinder. Record this weight $\underline{W}_s t$, on the record sheet.
15. Repeat steps 11 through 14 until equilibrium is reached or a maximum test time is obtained. Expand the time interval as maximum absorbency is approached. A suggested interval sequence is 0, 1, 2, 5, 10, 30, 60, and 90 minutes.

16. Measure the displaced piston height from the bottom of the cylinder. Record this height H on the record sheet.

17. Upon completion of the absorbency test, remove the piston and observe the condition of the material. Record the observation on the record sheet.

Calculations:

$W_f$ Weight of the absorbent material $W_c$ Dry weight of the combined cylinder $W_s t$ Wet weight of the combined cylinder at time, t $A_t$ Material absorbency under an external load at time, t A Maximum material absorbency under load.

Absorbency under an external load $$At = \frac{W_s t - W_c}{W_f}$$

$$A = (\max A^t)$$

The absorbency properties of representative examples of the present invention are shown below in Tables I and II.

Properties

In Example 1, F-75, a fine foundry sand, was covered with a preferred hydrogel forming polymer prepared from an aqueous solution of partially neutralized acrylic acid at a weight ratio of 45 parts filler core to 55 parts polymer.

Example 3 differed from Example 1 in weight ratio by using 55 parts filler core to 45 parts polymer. In Example 2, the polymer was not crosslinked and differed from Example 3 which was crosslinked.

TABLE II

| Absorbent Particle | Maximum Swell Capacity g saline/g | Swell Time to Gel seconds 10:1 |
| --- | --- | --- |
| Favor 800 (Stockhausen) | 47 | 25 |
| ASAP 1000 (Chemdal) | 40 | 29 |
| Example Number | | |
| 1. | 27 | 14 |
| 2. | 50+ | 32 |
| 3. | 23 | 24 |
| 4. | 40+ | 120 |
| 5. | 70+ | 9 |
| 6. | 70+ | 44 |
| 7. | 70+ | 85 |
| 8. | 25 | 27 |
| 9. | 41 | 4 |
| 10. | 50 | 2 |
| 20. | 21 | >5 min. |
| 21. | 33 | >5 min. |
| 24. | 31 | >5 min. |
| 25. | 32 | >5 min. |
| 28. | 11 | >5 min. |
| 29. | 22 | >5 min. |
| 30. | 26 | >5 min. |
| 31. | 34 | 7 |

TABLE III

| | Absorbency Under Load gm saline (1.0%) per gm | | | | |
| --- | --- | --- | --- | --- | --- |
| | 1 minute | 5 minutes | 10 minutes | 20 minutes | 30 minutes |
| Example 1 | 11 | 13 | 14 | 15 | — |
| Example 3 | 10 | 14 | 16 | 16 | 16 |
| Favor 800 | 7 | 11 | 15 | 20 | 23 |
| ASAP 1000 | 8 | 16 | 20 | 22 | — |
| Example 8 | 6 | 11 | 11 | 12 | 12 |
| Example 9 | 5 | 5 | 6 | 6 | 7 |
| Example 10 | 5 | 6 | 6 | 7 | |
| Example 11 | 10 | 18 | 20 | 21 | 22 |
| Example 20 | 3.5 | 5.3 | 5.8 | 6.1 | 6.5 |
| Example 21 | 1.4 | 2.6 | 3.2 | 3.7 | 4.1 |
| Example 28 | 1.6 | 1.9 | 2.0 | 2.0 | 2.1 |
| Example 29 | 1.1 | 2.1 | 2.1 | 2.9 | 2.9 |
| Example 30 | 1.3 | 2.3 | 2.7 | 3.3 | 4.0 |
| Example 31 | 6.4 | 8.3 | 9.5 | 11.2 | 12.3 |

The highly competitive performance in rate and absorbency under a load of the product of the present invention as seen from the data in Tables II and III are unexpected and represent an important advance in the art.

The complete adsorption of the polymerizing droplets onto the surface of the filler core was surprising and unexpected. During the course of the preparation it appeared that the filler particles became encapsulated during the early stages of the polymerization. This suggests certain theoretical explanations for the complete adsorption mentioned above. For example, early in the initiation of the polymerization, the soft and perhaps "sticky" droplets are attached to the filler core surface by secondary chemical forces or bonding provided at least in part by the chemical nature of the filler core particle surface. Additionally, the core particle surface may provide a sufficiently high surface energy to be readily wetted by the polymerizing droplets. In general, those physical-chemical phenomenon that tend to effect or control the adsorption and heterogenous reactions of liquids on solid surfaces influence the desired formation of the encapsulated core particles.

Absorbent Cores of Fiber and Superabsorbent Particles Examples 12–16

Cellulose pulp fibers were mixed with superabsorbent particles in a laboratory machine capable of providing a suitable air stream and collection screen to collect the mixture in the form of a soft, fluffy web.

FIG. 1 illustrates an absorbent core with a volume defined by the x, y, and z axis.

Figure 2:
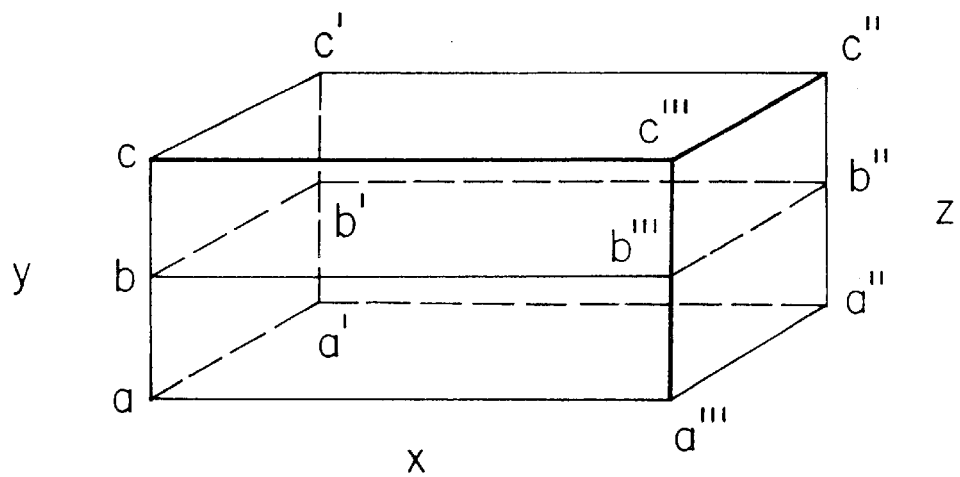
FIGS. 2–4 are diagrammatic representations of absorbent cores in accordance with the present invention showing various volumetric zones.

In FIG. 2, two volumetric zones are defined, one by the boundaries ab, a'b', a"b", and a'''b''' and a second by bc, b'c', b"c" , and b'''c'''.

Figure 3:
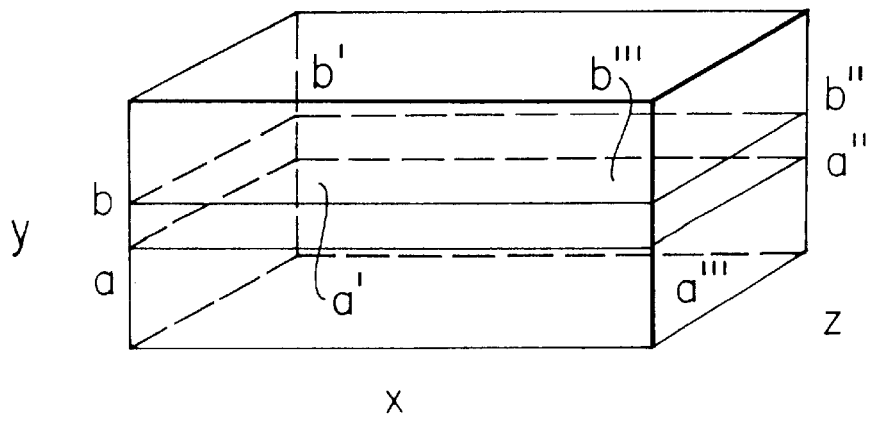
Figure 4:
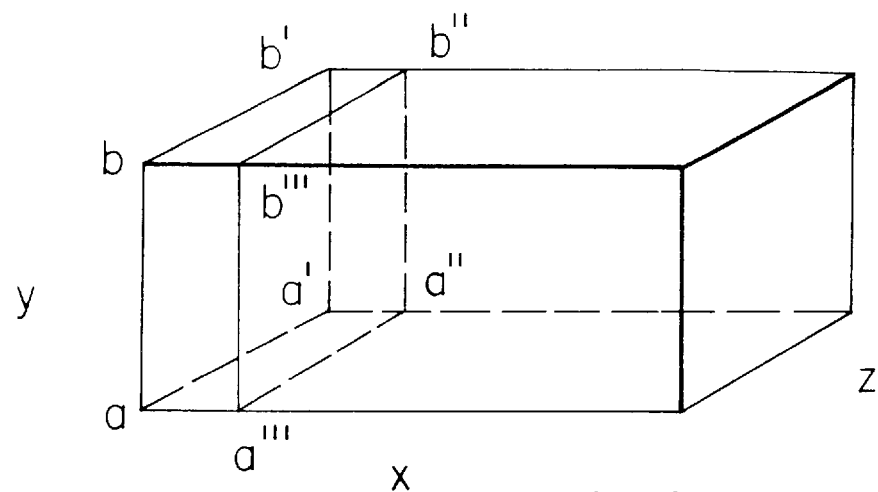

In FIGS. 3 and 4, the volumetric zone ab, a'b', a"b", and a'''b''' is defined.

The web of fiber and particles referred to herein as absorbent cores were approximately 9 inches in length, 4 inches in width, and after compression in a hydraulic press, 0.25 inch thickness. Referring to FIGS. 1 and 2, these dimensions are represented in an absorbent core by length "x," width "y," and thickness "z," respectively.

The absorbent cores of the present invention are defined by a series of planes, each of which is formed by the intersection of lines x and y moving in the z direction. These planes or any combination of multiples of planes provide volumetric zones (e.g., referring to FIG. 3, showing a volumetric zone ab, a'b', a"b", a'''b''' and FIG. 4 showing a zone ab, a'b', a"b", a'''b''') which are comprised of fiber, particles of the present invention, and air. These zones can occupy at least about 2% of the volume of an absorbent device in the dry state. Since the absorbent particles of the present invention are each individually comprised of a filler core and a superabsorbent polymer in the weight range of preferably about 30 to 70 to 70 to 30, it follows that the aforementioned volumetric zones are comprised of four components; namely, fiber, air, superabsorbent polymer, and filler. Furthermore, these components may be varied in both ratio and location in the core, thus providing a new degree of freedom in design of absorbent cores which may be optimized for both functionality and cost. The foregoing discussion on the particle composition and other variables associated with the particles the present invention clearly shows the enormous magnitude design options available with this new particle in bination with fiber and void space in the absorbent core.

Table IV lists the composition and properties of several examples of absorbent cores containing a) pulp fibers; and b) SAP and/or absorbent particles of the present invention.

ing major improvements in leakage prevention through the presence of more available SAP surface area (i.e., a greater number of absorbent particles of the present invention can be made with the same amount of SAP used in present commercial absorbent devices).

Figure 7:
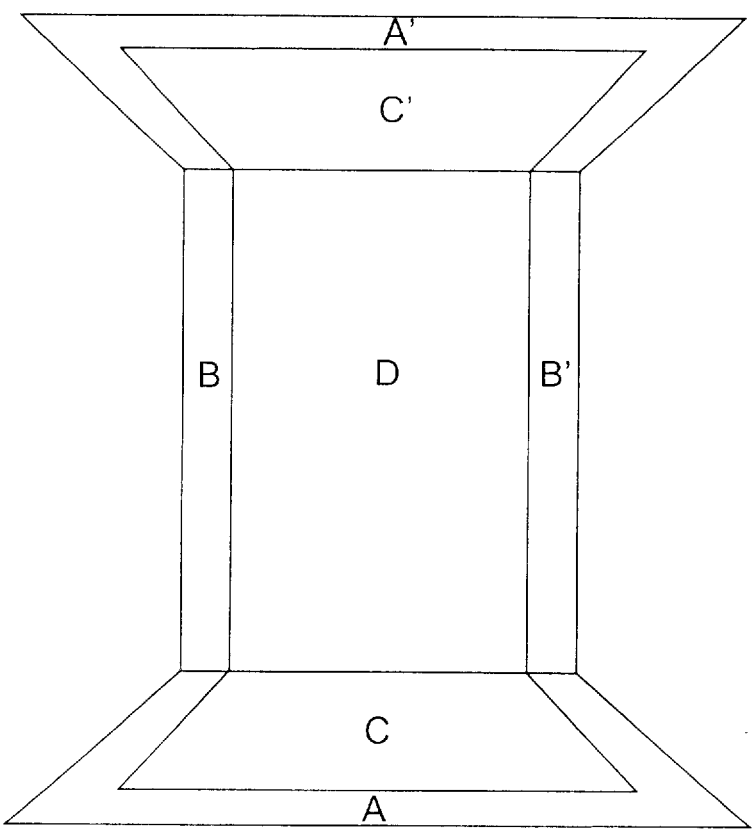
FIG. 7 is a diagrammatic representation of an absorbent device showing various zones.

Alternatively, an absorbent device of FIG. 7 may be designed with high capacity particles as in Example 5 and located in the more inward zone D where control of large amounts of localized fluid is needed. As in the discussion above, such an improvement can be achieved without additional cost by using increased amounts of the lower cost particles of the present invention.

The absorbent particles of the present invention can be used in all types of absorbent devices where commercially available SAP particles are used. The absorbent particles of the present invention can fully or partially replace the commercially available SAP particles in absorbent devices

TABLE IV

Absorbent Core Properties

| Ex. | Absorbent Core Wt (gms) | Wt % SAP and/or Absorbent Particle | SAP and/or Particle Composition | Time to Absorb 40 ml Saline, Successive Insults Seconds | | | | Rewet (gm) | Capacity (gm) |
| --- | --- | --- | --- | --- | --- | --- | --- | --- | --- |
| | | | | 1 | 2 | 3 | 4 | | |
| 12 | 18.0 | 50 | ASAP-1000 | 8 | 21 | 55 | 90 | 7.6 | — |
| 13 | 19.5 | 30 | ASAP-1000 | 6 | 11 | 27 | 40 | 8.5 | — |
| 14 | 20.3 | 40 | Example 1 (4 pbw) ASAP-1000 (1 pbw) | 7 | 21 | 31 | 53 | 7.7 | |
| 15 | 18.8 | 40 | ASAP-1000 | — | — | — | — | — | 363 |
| 16 | 19.1 | 40 | Example 1 (4 pbw) ASAP-1000 (1 pbw) | — | — | — | — | — | 337 |

From the data in Table IV, it is shown that with the absorbent particles of the present invention, it is now possible to more closely optimize cost and performance in an absorbent device particularly with respect to performance attributes of capacity and rate.

More specifically, the data in Table III provides the basis for the design of absorbent devices with unique and heretofore unachievable properties without significant cost increases.

For example, in the device shown in FIG. 7, a number of zones are indicated, each of which may have special importance due to location, in providing the desired functions of leakage prevention, providing a dry surface to the wearer, and reduction in bulk through replacement of pulp with SAP particles; and, importantly to achieve these at low cost.

The absorbent core of Example 14 contains 8.1 gm of SAP particles of which 1.6 gm are 100% superabsorbent polymer ASAP 1000. The remaining 6.5 gm of particles (Example 1) contain 56% SAP by weight or 3.6 gm SAP giving a total amount of SAP of 5.2 gm. In comparison with Example 12 which contains 9.0 gms of superabsorbent, the rate of absorption and surface dryness are significantly improved for the rate of absorption and roughly equivalent for surface dryness. These improvements are achieved at a significant reduction in raw material cost.

Absorbent devices such as that shown in FIG. 7 may thus be optimized by the presently disclosed particles by employing, e.g., 75–100% more absorbent particles in, for example, zones A,A', B,B', and optionally C,C' thus achievsuch as those described in U.S. Pat. Nos. 5,019,063; 5,300,358; 4,324,247; 4,342,314; 4,634,440; 5,074,856; and 4,944,735, all incorporated herein by reference in their entireties.

As shown in Table IV, for example, particles of the present invention can be blended with commercially available superabsorbent polymers to achieve a wide range of cost and performance. For instance, commercially available SAP particles can be combined with absorbent particles of the present invention in weight ratios of from about 1:9 to about 9:1. In addition, when the absorbent particles are used in an absorbent device such as a diaper or sanitary napkin, the hydrophilic fibers and absorbent particles are present in a weight ratio of from about 95:5 to about 2:3.

Techniques to increase the ratio of surface area to mass by forming aggregates of small SAP particles as taught, for example, in U.S. Pat. No. 5,180,622 (Berg), or by incorporating blowing agents as for example in U.S. Pat. No. 5,118,719 (both incorporated herein by reference) are applicable to the present invention as well with the added advantage of significantly reduced cost due to the filler core.

Example 17

In Examples 17 and 18, superabsorbent granules of the present invention were prepared by the general procedure of Example 1 with a silica content of 50% by weight.

To illustrate the highly cost effective performance of the present invention, female sanitary napkins were prepared according to the teachings of U.S. Pat. No. 4,950,364, entitled "Thin, Flexible Sanitary Napkin" which is incorporated herein by reference. In particular, the present embodiment seeks to achieve a sanitary napkin which is thin and flexible and which is absorbent enough to absorb and contain medium to high menstrual flows.

Specifically, a laminate was prepared comprising a layer of airlaid bonded pulp sheet material having a thin film of pressure sensitive adhesive on one surface. The high performance superabsorbent granules of the present invention were uniformly sprinkled on the adhesive layer which had either a light (approximately ½ mil), medium (approximately 1 mil) or heavy (approximately 1½ mil) amount of adhesive, and then the sheet material was G folded into a laminate about 55 mm in width so that the superabsorbent granules were located within the inner folds of the laminate. Next the laminate was interposed between a fluid transfer layer of airlaid pulp sheet material and a polyethylene barrier film.

A topsheet comprising a polyethylene film having three dimensional apertures was positioned on the outer face of the transfer layer airlaid material. The edges were sealed giving a sanitary napkin having a length of about 225 mm, a width of 70–100 mm, and a thickness of about 2.75 mm.

For comparative purposes, napkins were prepared with a commercial grade of superabsorbent (ASAP 1100, Chemdall) comprising granules of 100% superabsorbent polymer.

Table V below illustrates the absorbing properties of napkins containing the novel polymer sheath, absorbent particles of the present invention having only 50% by weight SAP and 50% by weight of silica.

TABLE V

| Super Absorbent Polymer Granules | Adhesive; Application | Quantity, Granules Per Pad; GM | Absorbency Rate: Sec. | Rewet; GM | Stain; MM | Capacity; GM |
|---|---|---|---|---|---|---|
| Present Invention | Fuller* 8130; Light | 0.80 | 2.80 | 2.20 | 78.00 | 44.00 |
| | Fuller 8130; Light | 1.00 | 3.10 | 0.20 | 80.00 | 46.50 |
| | Fuller 8130; Light | 1.20 | 3.00 | 0.00 | 78.00 | 51.30 |
| | Fuller 8130; Med. | 0.80 | 3.10 | 0.00 | 75.00 | 41.70 |
| | Fuller 8130; Med. | 1.00 | 2.90 | 0.00 | 78.00 | 45.50 |
| | Fuller 8130; Med. | 1.20 | 3.00 | 0.00 | 80.00 | 53.00 |
| | Fuller 8130; Heavy | 0.80 | 3.20 | 0.19 | 75.00 | 42.30 |
| | Fuller 8130; Heavy | 1.00 | 3.00 | 0.00 | 80.00 | 44.90 |
| | Fuller 8130; Heavy | 1.20 | 3.00 | 0.00 | 80.00 | 49.20 |
| ASAP-1100 | Fuller 8130; Light | 0.80 | 2.90 | 0.00 | 78.00 | 42.80 |
| | Fuller 8130; Light | 1.00 | 2.60 | 0.00 | 78.00 | 47.90 |
| | Fuller 8130; Light | 1.20 | 2.50 | 0.00 | 80.00 | 52.30 |
| | Fuller 8130; Med. | 0.80 | 2.70 | 0.00 | 75.00 | 43.40 |
| | Fuller 8130; Med. | 1.00 | 2.60 | | 75.00 | 50.20 |
| | Fuller 8130; Med. | 1.20 | 2.50 | 0.60 | 90.00 | 55.00 |
| | Fuller 8130; Heavy | 0.80 | 2.60 | 0.30 | 80.00 | 42.30 |
| | Fuller 8130; Heavy | 1.00 | 2.50 | | 75.00 | 50.20 |
| | Fuller 8130; Heavy | 1.20 | 2.70 | 0.00 | 75.00 | 52.40 |
| Present Invention | NS 8423-23-4**; Light | 0.80 | 2.40 | 0.28 | 78.00 | 54.60 |
| | NS 8423-23-4; Light | 1.00 | 2.30 | 0.00 | 72.00 | 57.90 |
| | NS 8423-23-4; Light | 1.20 | 2.30 | 0.00 | 72.00 | 62.90 |
| | NS 8423-23-4; Med. | 0.80 | 2.40 | 1.60 | 80.00 | 57.30 |
| | NS 8423-23-4; Med. | 1.00 | 2.60 | 0.00 | 72.00 | 58.40 |
| | NS 8423-23-4; Med. | 1.20 | 2.70 | 0.00 | 75.00 | 63.80 |
| | NS 8423-23-4; Heavy | 0.80 | 2.60 | 3.30 | 77.00 | 55.30 |
| | NS 8423-23-4; Heavy | 1.00 | 2.80 | 0.00 | 80.00 | 58.10 |
| | NS 8423-23-4; Heavy | 1.20 | 2.50 | 0.00 | 85.00 | 60.30 |
| ASAP-1100 | NS 8423-23-4; Light | 0.80 | 1.80 | 0.36 | 82.00 | 58.70 |
| | NS 8423-23-4; Light | 1.00 | 1.90 | 0.23 | 80.00 | 68.30 |
| | NS 8423-23-4; Light | 1.20 | 2.00 | 0.00 | 78.00 | 71.70 |
| | NS 8423-23-4; Med. | 0.80 | 2.40 | 1.60 | 80.00 | 57.30 |
| | NS 8423-23-4; Med. | 1.00 | 2.60 | 0.00 | 82.00 | 64.20 |
| | NS 8423-23-4; Med. | 1.20 | 2.20 | 0.00 | 78.00 | 70.00 |
| | NS 8423-23-4; Heavy | 0.80 | 2.50 | 0.00 | 85.00 | 57.50 |
| | NS 8423-23-4; Heavy | 1.00 | 2.40 | 0.00 | 78.00 | 55.60 |
| | NS 8423-23-4; Heavy | 1.20 | 2.20 | 0.34 | 78.00 | 70.20 |

*H. B. Fuller Co. (St. Paul, MN)
**National Starch & Chemical Corp. (Bridgewater, N.J.)

Example 18

In another embodiment of the present invention, a thick, fluffy absorbent pad comprising a combination of cellulose pulp fluff and superabsorbent granules were prepared and evaluated by laboratory fluid absorption tests.

The pads tested in this experiment were about 260 mm long, 60–70 mm wide, and 20 mm thick. The construction specifically comprised four layers of fluff pulp formed by "G" folding a "blanket layer" of pulp (7.8 gm) around an embossed and densified layer of pulp (4.1 gm). The pad further comprised a topsheet of thermally bonded polypropylene, a polyethylene fluid backsheet, and a resin bonded web of crimped PET stable fiber interposed between the topsheet and the fluff core. Superabsorbent granules were uniformly dispersed within the core through a salt shaker. In the case of the present invention, 1.4 gm of absorbent particles were distributed on the upper side of the embossed layer and 3.0 gm on the lower side. As a comparative example, Chemdall ASAP 1000 superabsorbent granules were similarly positioned, 1.0 gm being placed on the upper side and 3.0 gm on the lower side.

Absorption properties are summarized in Table VI.

Pads of this general construction are useful in feminine hygiene in the control of menstrual fluid as well as for the absorption and control of urine in light to moderate episodes of urinary incontinence.

TABLE VI

|  | Absorption Rate First 20 ml. Seconds | Absorption Rate Second 20 ml. Seconds | Rewet gm | Capacity gm |
|---|---|---|---|---|
| Present Invention | 1.00 | 2.30 | 1.20 | 235.00 |
| ASAP-1000 | 1.00 | 1.80 | 1.80 | 243.00 |

In Examples 17 and 18, absorbency rate, rewet, stain, and capacity were obtained as follows:

Absorbency Rate was determined as follows:

Apparatus: One 4"×4" Lucite cylinder block with a 1" diameter opening in center of block; 1% dyed saline solution; stopwatch (to record elapsed time in seconds graduated to 0.1 second).

Procedure: Lay the sanitary product having a plastic film, absorbent core and cover sheet flat, so that it is free from wrinkles and folds, with the cover sheet up. Place the cylinder block in the center of the product with the cover sheet up. Measure 10 ml of 1% saline solution into the graduated cylinder. Pour 10 ml 1% saline solution from graduated cylinder onto product through opening in lucite block and immediately start the stopwatch. Allow the solution to flow onto the surface of the sanitary product.

Stop the stopwatch as soon as the solution is completely absorbed. Record the absorption time for five specimens to the nearest 0.1 second. Determine the average absorption time for five specimens to the nearest 0.1 second. Average absorption time in seconds to the nearest 0.1 second and fluid volume.

Rewet was determined as follows:

Apparatus: One 4"×4" Lucite cylinder block with a 1" diameter opening in center block; dyed 1% saline solution; VWR Filter paper, Grade #417, 9 cm in diameter or equivalent; flat plate weighing 0.05 kgs (4"×4"×⅛ Lucite square); 2.2 kilogram weight; 25 ml capacity cylinder; and top loading electronic balance, accurate to ±0.01 g.

Procedure: Prepare five products for testing by placing flat on a level surface. Center the cylinder block on the coversheet of the product. Pour 10 ml of 1% saline solution into the cylinder block opening. Remove the cylinder block and allow the product to stand for 5 minutes. Weigh 10 filter papers and record weight. After 5 minutes, simultaneously place the weighed filter paper, clear Lucite plate, and 2.2 kilogram weight (approx. 0.5 psi) on the center of the product. Leave in this position for 15 seconds. Remove the weight and plate and weigh the filter papers. Determine the average rewet for five samples as follows: Final Filter Paper Weight (g) minus Initial Filter Paper Weight (g) equals Rewet (g).

Stain was determined as follows:

Apparatus: One 4"×4" Lucite cylinder block with a 1" diameter opening in center of block; dyed (1%) saline solution; 10 ml graduated cylinder; stopwatch (accurate to ±0.1 second); and steel ruler measuring 30 cm in length and graduated in 1 mm.

Procedure: Place cylinder block on the center of the coversheet, top side of the pad. Pour 10 ml of 1% saline solution into the cylinder block opening and allow the fluid to be absorbed. Remove the cylinder block as soon as absorption is complete. Allow the product to absorb the fluid. After two minutes, measure (in millimeters) the length of the stain from the furthest two points, keeping the ruler parallel to the length of the product. Average the readings from 5 samples and report in millimeters.

Total capacity was determined as follows:

Apparatus: Triple beam balance or top loading electronic balance (accurate to ±0.1 gm); 0.9% saline solution; blotters (4"×4" pulp board—ITT Rayonier PMXE); Whatman Filter paper, grade #1, or equivalent; Ohaus calibration weights of 1170.4 gm, ±0.4 gms (or equivalent); stopwatch; thermometer; Plexiglass® template measuring 4.75×14.0 cm; and nonwoven sample piece measuring 8"×12".

Procedure: Record dry weight of sample piece without release tape. Wrap sample in nonwoven piece. Submerge sample piece in 0.9% saline (25° C.) solution for 10 minutes. Drain for 2 minutes in a vertical position. Unwrap nonwoven from sample. Place 4"×4" pulp square under bottom surface of saturated sample, poly side of product facing up. Place template with controlled weight onto product for 30 seconds. Continue above step until rewet value is less than 0.5 gm. Record weight of wet sample piece.

$$\frac{\text{Wet Weight Sample} - \text{Release Tape}}{\text{Dry Weight Sample} - \text{Release Tape}} = \text{Total Capacity Value}$$

Example 19

A portion of the product from Example 5 remaining on a #30 mesh screen was ground lightly with a mortar and pestle and then combined with the portion that had passed through the screen. Using Nos. 30, 60, and 140 mesh screens, the particle size distribution of the combined material was determined and compared to the F-75 silica core material. This comparison shown in Table VII clearly illustrates the high degree of predictability of particle size offered by the present invention.

TABLE VII

|  | Silica F-75, Wt. % | Example 5, Wt. % |
|---|---|---|
| Less than 100 microns | 7 | 10 |
| Less than 150, greater than 100 microns | 22 | — |
| Greater than 150, less than 300 microns | 65 | — |
| Greater than 300 microns | 6 | — |
| Greater than 100, less than 260 microns | — | 26 |
| Greater than 260, less than 700 microns | — | 64 |

Example 20

$CaCO_3$ filler with surface crosslink

A 2000 ml round bottom flask equipped with nitrogen inlet and outlet tubes, a reflux condenser, a Dean Stark trap, a mechanical stirrer, a thermometer, and an addition funnel was purged with nitrogen. 800 ml cyclohexane, and 4.32 g Span 60 (HLB value 4.7) were added to the flask and the internal temperature brought to 42° C. with stirring to disperse the Span 60. After approximately 10 minutes, the contents of the flask were allowed to cool to room temperature.

Meanwhile, 80 ml acrylic acid and 10 ml de-ionized distilled water were stirred in a 500 ml round bottom flask and cooled by an ice bath. While cooling, 33.5 grams of sodium hydroxide dissolved in 100 ml de-ionized distilled water were added dropwise to the acrylic acid solution. 128 mg potassium persulfate in 10 ml de-ionized distilled water were added to the partially neutralized acrylic acid solution. The mixture was stirred for approximately 10 minutes with cooling from the ice bath. 102.4 grams of calcium carbonate (Hubercarb Q 20 60) were added to the cyclohexane/surfactant solution. The sodium acrylate solution was added with vigorous stirring.

The temperature of the reaction mixture was brought to 55° C. and held there for 6 hours. The water and cyclohexane azeotrope were distilled over until 90 ml of water had collected. The mixture was allowed to cool overnight under nitrogen atmosphere.

The next morning, 1.34 g of ethylene glycol diglycidyl ether was added and the reaction mixture was heated to 55° C. for 7 hours under nitrogen atmosphere, then allowed to cool overnight. The remaining water was removed with the water/cyclohexane azeotrope to give 190 g of off white granular material.

Example 21

Silica F-75 filler with internal crosslink

A 2000 ml round bottom flask equipped with nitrogen inlet and outlet tubes, a reflux condenser, a Dean Stark trap, a mechanical stirrer, a thermometer, and an addition funnel was purged with nitrogen. 800 ml cyclohexane, and 4.32 g Span 60 (HLB value 4.7) were added to the flask and the internal temperature brought to 42° C. with stirring to disperse the Span 60. After approximately 10 minutes, the contents of the flask were allowed to cool to room temperature.

Meanwhile, 80 ml acrylic acid and 10 ml de-ionized distilled water were stirred in a 500 ml round bottom flask and cooled by an ice bath. While cooling, 33.5 grams of sodium hydroxide dissolved in 100 ml de-ionized distilled water were added dropwise to the acrylic acid solution. 96 mg of N,N'-methylene-bis-acrylamide were added to the aqueous solution and were stirred until dissolved. 128 mg potassium persulfate in 10 ml de-ionized distilled water were then added to the partially neutralized acrylic acid solution. The mixture stirred for approximately 10 minutes with cooling from the ice bath.

102.4 grams of silica (U.S. Silica, F-75) were added to the cyclohexane/surfactant solution. The sodium acrylate solution was added with vigorous stirring. The temperature of the reaction mixture was brought to 55° C. and held there for 6 hours. The water and cyclohexane azeotrope were distilled over until 115 ml of water had collected. The solid product was collected and dried to give 191 g of white granular material.

Example 22

Silica F-75 filler control, no crosslinking

A 2000 ml round bottom flask equipped with nitrogen inlet and outlet tubes, a reflux condenser, a Dean Stark trap, a mechanical stirrer, a thermometer, and an addition funnel were purged with nitrogen. 800 ml cyclohexane and 4.32 g Span 60 (HLB value 4.7) were added to the flask and the internal temperature brought to 42° C. with stirring to disperse the Span 60. After approximately 10 minutes, the contents of the flask were allowed to cool to room temperature.

Meanwhile 80 ml acrylic acid and 10 ml de-ionized distilled water were stirred in a 500 ml round bottom flask and cooled by an ice bath. While cooling, 33.5 grams of sodium hydroxide dissolved in 120 ml de-ionized distilled water were added dropwise to the acrylic acid solution. 128 mg potassium persulfate in 10 ml de-ionized distilled water were added to the partially neutralized acrylic acid solution. The mixture was stirred for approximately 10 minutes with cooling from the ice bath.

102.4 grams of silica (U.S. Silica, F-75) were added to the cyclohexane/surfactant solution. The sodium acrylate solution was added with vigorous stirring. The temperature of the reaction mixture was brought to 55° C. and held there for 6 hours. The water and cyclohexane azeotrope were distilled over until 114 ml of water had collected. The solid product was collected and dried to give 195 g of white granular material.

Example 23

Molecular Weight Control

A 2000 ml three necked round bottom flask equipped with a mechanical stirrer, thermometer, Dean Stark apparatus, reflux condenser, and a nitrogen inlet was purged with nitrogen. 800 ml of cyclohexane and 4.32 g of Span 60 (ICI Americas, Inc., Wilmington, Del.) were added to the flask and allowed to dissolve. After 10 minutes of stirring, the reaction mixture was homogeneous.

Meanwhile, 80 ml acrylic acid and 33.42 g of sodium hydroxide dissolved in 120 ml $H_2O$ were mixed together in an ice bath over a 5 minute period of time.

102.4 g of Ottawa fine foundry sand with an AFS grain size of 75 were added to the cyclohexane/surfactant solution. The sodium acrylate solution and 2.0 μl of 3-mercapto-1,2-propanediol (chain transfer agent for molecular weight control) were added with vigorous stirring. 128 mg of potassium persulfate were added and the temperature of the reaction mixture was brought to 50° C. for 1 hour. The temperature was increased to 60.5° C. for 5 hours. Water was removed as an azeotrope with cyclohexane and particles of the present invention were isolated. The polymer resulting from the chain transfer reaction had a number average molecular weight of 256,000, which was 60% smaller than the polymer isolated from an identical polymerization (?) that did not employ a chain transfer agent.

Example 24

Large Particle Size Silica Filler, on 60 mesh, >250 microns

A 2000 ml three necked round bottom flask equipped with a mechanical stirrer, thermometer, Dean Stark apparatus, reflux condenser, and a nitrogen inlet was purged with nitrogen. 800 ml of cyclohexane and 4.32 g of Span 60 (ICI Americas, Inc., Wilmington, Del.) were added to the flask and allowed to dissolve. After 10 minutes of stirring, the reaction mixture was homogeneous.

Meanwhile, 80 ml acrylic acid and 33.42 g of sodium hydroxide dissolved in 120 ml $H_2O$ were mixed together in an ice bath over a 5 minute period of time.

102.4 g of larger than 60 mesh (250 microns and greater) Ottawa fine foundry sand with an AFS grain size of 75 were added to the cyclohexane/surfactant solution. The sodium acrylate solution was added with vigorous stirring. 128 mg of potassium persulfate were added and the temperature of the reaction mixture was brought to 50° C. for 1 hour. The temperature was then increased to 60.5° C. for 5 hours. Water was removed as an azeotrope with cyclohexane resulting in 181.3 g of particulate product.

Example 25

Small Particle size silica filler, 100–200 mesh, 75–150 microns

A 2000 ml round bottom flask equipped with nitrogen inlet and outlet tubes, a reflux condenser, a Dean Stark trap, a mechanical stirrer, a thermometer, and an addition funnel was purged with nitrogen. 800 ml cyclohexane and 4.32 g Span 60 (HLB value 4.7) were added to the flask and the internal temperature brought to 42° C. with stirring to disperse the Span 60. After approximately 10 minutes, the contents of the flask were allowed to cool to room temperature.

Meanwhile, 80 ml acrylic acid and 20 ml de-ionized distilled water were stirred in a 500 ml round bottom flask and cooled by an ice bath. While cooling, 33.5 grams of sodium hydroxide dissolved in 100 ml de-ionized distilled water were added dropwise to the acrylic acid solution. 128 mg potassium persulfate in 10 ml de-ionized distilled water were added to the partially neutralized acrylic acid solution. The mixture stirred for approximately 10 minutes with cooling from the ice bath. 102.4 grams of silica (U.S. Silica, F-110, previously screened to 100–200 mesh) were added to the cyclohexane/surfactant solution. The sodium acrylate solution was added with vigorous stirring. The temperature of the reaction mixture was brought to 55° C. and held there for 6 hours. The water and cyclohexane azeotrope was distilled over until 115 ml of water had collected. The solid product was collected and dried to give 174 g of off-white granular material.

Example 26

Hardwood particles filler

A 2000 ml three necked round bottom flask equipped with a mechanical stirrer, thermometer, Dean Stark apparatus, reflux condenser, and a nitrogen inlet were purged with nitrogen. 800 ml of cyclohexane and 4.32 g of Span 60 (ICI Americas, Inc., Wilmington, Del.) were added to the flask and allowed to dissolve. After 10 minutes of stirring, the reaction mixture was homogeneous.

Meanwhile, 80 ml acrylic acid and 33.42 g of sodium hydroxide dissolved in 120 ml $H_2O$ were mixed together in an ice bath over a 5 minute period of time.

50 g of 60 mesh hardwood flour (Composition Materials of America, Inc.) were added to the cyclohexane/surfactant solution. The sodium acrylate solution was added with vigorous stirring. 128 mg of potassium persulfate were added and the temperature of the reaction mixture was brought to 50° C. for 1 hour. The temperature was then increased to 60.5° C. for 5 hours. Water was removed as an azeotrope with cyclohexane resulting in 139.0 g of particulate product.

Example 27

Walnut shell particulate filler

A 2000 ml three necked round bottom flask equipped with a mechanical stirrer, thermometer, Dean Stark apparatus, reflux condenser, and a nitrogen inlet was purged with nitrogen. 800 ml of cyclohexane and 4.32 g of Span 60 (ICI Americas, Inc., Wilmington, Del.) were added to the flask and allowed to dissolve. After 10 minutes of stirring, the reaction mixture was homogeneous.

Meanwhile, 80 ml acrylic acid and 33.42 g of sodium hydroxide dissolved in 120 ml $H_2O$ were mixed together in an ice bath over a 5 minute period of time.

50 g of 100 mesh Walnut Shell flour (Composition Materials of America, Inc.) were added to the cyclohexane/surfactant solution. The sodium acrylate solution was added with vigorous stirring. 128 mg of potassium persulfate were added and the temperature of the reaction mixture was brought to 50° C. for 1 hour. The temperature was increased to 60.5° C. for 5 hours. Water was removed as an azeotrope with cyclohexane resulting in 100.3 g of particles of the present invention.

Example 28

Surface Crosslinking by Calcium Ions 10.0 g of encapsulated particles from Example 22 and 30 ml of cyclohexane were added to 100 ml round bottom flask equipped with a magnetic stir bar, Dean Stark apparatus, and reflux condenser. 1.8 g of calcium chloride dissolved in 5 ml of $H_2O$ were then added with vigorous stirring. The reaction mixture was stirred for 2 hours and water was removed as an azeotrope with cyclohexane. The resulting product was analyzed and determined to have surface crosslinking.

Example 29

Surface Crosslinking by Calcium Ions 10.0 g of encapsulated particles from Example 22 were added to 100 ml round bottom flask equipped with a magnetic stir bar, Dean Stark apparatus, and reflux condenser. 1.8 g of calcium chloride dissolved in 20 ml of $H_2O$ were then added with vigorous stirring. The reaction mixture was stirred for 2 hours. 20 ml of cyclohexane were added and the water was removed as an azeotrope with cyclohexane. The resulting product was analyzed and determined to have surface crosslinking.

Example 30

Surface Crosslinking by Magnesium Ions 10.0 g of encapsulated particles from Example 22 and 30 ml of cyclohexane were added to a 100 ml round bottom flask equipped with a magnetic stir bar, Dean Stark apparatus, and reflux condenser. 3.6 g of magnesium chloride dissolved in 5 ml of $H_2O$ were then added with vigorous stirring. The reaction mixture was stirred for 2 hours and water was removed as an azeotrope with cyclohexane. The resulting product was analyzed and determined to have surface crosslinking.

Example 31

Twelve grams of Example 21 (silica coated with poly sodium acrylate:acrylic acid 75:25), 25 ml of methanol, 40.5 mg of ethyleneglycol diglycidyl ether, and 1.5 g of distilled water were placed in a 100 ml flask and heated to reflux for seven hours. The reaction mixture was poured into a crystallizing dish and dried under a heat lamp for 2 hours then in a 70° C. oven for 1 hour. Example 31 is a white granular material weighing 11.6 g.

Example 32

In the following procedures, particle attrition was measured under selected conditions of mechanical agitation.

Absorbent particles of the present invention having a silica based core and a polyacrylate SAP coating wherein core and SAP are present in a 1:1 weight ratio were first presieved to obtain particles in a selected particle size range of 250 to 520 microns. After subjecting the particles to mechanical agitation, analysis for the presence of fractured or separated polymer present as particles less than 74 microns in size was conducted as listed below:

| Method of Agitation | Weight % less than 74 microns |
|---|---|
| Shaker | 0.0 |
| Rolling with Small Pellets | 0.2 |
| Rolling with Large Pellets | 0.1 |

The above methods of agitation were conducted as follows:

Condition 1. Paint Shaker 10 grams of super absorbing polymer were placed in a 170 ml cylindrical metal container. This container was in turn placed in a 1 gallon paint can and placed on a paint shaker for 60 minutes. At the end of this time, the material was removed and analyzed for particle size distribution using a standard set of sieves.

Condition 2. Small Burundum Rollers 10 grams of super absorbing polymer were placed in a 170 ml cylindrical metal container along with 4 cylindrical Burundum pellets of 13 mm diameter by 13 mm in length. This container was in turn placed in a 1 gallon paint can and placed on a paint roller for 30 minutes. At the end of this time, the material was removed and analyzed for particle size distributing using a standard set of sieves.

Condition 3. Large Burundum Rollers 10 grams of super absorbing polymer were placed in a 170 ml cylindrical metal container along with 2 cylindrical Burundum pellets of 21 mm diameter by 21 mm in length. This container was in turn placed in a 1 gallon paint can and placed on a paint roller for 30 minutes. At the end of this time, the material was removed and analyzed for particle size distributing using a standard set of sieves.

Based on the above results, the absorbent particles of the present invention exhibit fracture-resistant qualities based, in part, on the "weight % less then 74 microns" results. This shows highly acceptable levels of adhesion of the polymer to the solid core.

Example 33

Particle Size Control

To illustrate the predictable and controllable absorbent particle size achievable within the teachings of the present invention, the following embodiments are provided.

Absorbent particles were prepared according to Example 24, wherein silica particles prescreened to a particle size range of about 250 to 300 microns were coated with a polyacrylic acid—sodium polyacrylate at a 1:1 weight ratio of silica to polymer.

These conditions were repeated with absorbent particles prepared according to Example 25 with a silica core particle having a particle size range of about 75 microns to 150 microns.

Both granular products were lightly ground in a Braun CA Model grinder and then subjected to a series of sieves to separate the particles according to size. Data for this procedure is shown in Table VIII.

TABLE VIII

| Sieve | | | | Weight | % Fiber | Median | Coating |
|---|---|---|---|---|---|---|---|
| Mesh Size | Particle Size $\mu$ | Weight on screen g | thru screen g | Than By Weight | Particle Size $\mu$ | Thickness T, $\mu$ |
| Example 24 | | | | | | |
| 40 | 420 | 22.7 | 22.3 | 50 | 240 | 60–85 |
| 60 | 250 | 15.9 | 6.4 | 14 | | |
| 100 | 150 | 3.95 | 2.4 | 5 | | |
| 200 | 75 | 1.6 | 0.8 | 1.7 | | |
| Example 25 | | | | | | |
| 40 | 420 | 4.2 | 40.8 | 90.6 | 310 | 80–117 |
| 60 | 250 | 27.7 | 13.1 | 29.1 | | |
| 100 | 150 | 8.2 | 4.9 | 10.9 | | |
| 200 | 75 | 3.5 | 1.4 | 3.1 | | |

Example 34

Cyclohexane (850 ml), Tween 81® (3.30 g) and Span 60® 1.10 g) were placed in a 2L resin kettle equipped with a mechanical stirrer, Teflon® stir paddle, thermometer, condenser, and a nitrogen inlet. This surfactant system has an HLB of 8.7. In a 500 ml Erlenmeyer flask, sodium hydroxide (41.5 g) was dissolved in water (140 ml). The aqeous hydroxide solution was cooled to 5° C. and acrylic acid 95.0 ml) was added. The sodium acrylate solution was introduced into the resin kettle and the reaction vessel was purged with nitrogen. Potassium persulfate (145 mg) was added to initiate the polymerization. One hour after the polymerization was initiated, U.S. Silica F-75 (83.0 g) was introduced into the resin kettle through a powder funnel over a 5 minute period. The increased viscosity of the polymerization aided in the suspension of the silica. The silica was dispersed uniformly throughout the reaction mixture. After 2 hours, the polymerization formed discrete particles and ethylene glycol diglycidyl ether (335 mg) was added. The reaction was refluxed for 1 hour and the resultant product was dried in a rotary dryer for 1 hour at 100° C. Ninety percent of the product consisted of discrete particles ranging in size from 150–600 microns.

Absorbent particles typified by the process of Example 34 have the following properties:

| Ratio of polymer to water-resistant solid core | 3:2 |
|---|---|
| Absorbent particle size range | 150–800 microns |
| Absorbency under a load | 15–20 gm |
| Time to gel, seconds | 10–30 |
| Capacity | 20–30 gm |

Other embodiments of the present invention will be apparent to those skilled in the art from consideration of the specification and practice of the present invention disclosed herein. It is intended that the specification and examples be considered as exemplary only, with a true scope and spirit of the present invention being indicated by the following claims.

What is claimed is:

1. A method for preparing a plurality of individual and discrete absorbent particles comprising the steps of:
   a) suspending an aqueous solution comprising an ethylenically unsaturated monomer capable of polymerization into a hydrogel forming polymer and an initiator in a water immiscible solvent in the presence of a surface active agent;

b) initiating the polymerization of the ethylenically unsaturated monomer while suspended in said water immiscible solvent; and c) co-suspending water resistant solid core particles in said water immiscible solvent for a time sufficient to permit the individual and substantial encapsulation of the water resistant solid core particles by said hydrogel forming polymer to form said absorbent particles.

2. The method of claim 1, further comprising the step of removing all or a portion of any water present in said absorbent particles by azeotropic distillation.

3. The method of claim 1, further comprising isolating said absorbent particles formed and removing any water present in said particles by heating.

4. The method of claim 1, further comprising cross-linking the surface of the absorbent particle formed in step c).

5. The method of claim 4, further comprising the step of removing all or a portion of any water present in said absorbent particles by azeotropic distillation.

6. The method of claim 4, further comprising isolating said absorbent particles formed and removing any water present in said particles by heating.

7. The method of claim 1, wherein said hydrogel forming polymer has a coating thickness of from about 2 $\mu$ to about 3000 $\mu$.

8. The method of claim 7, wherein said coating thickness is from about 10 $\mu$ to about 300 $\mu$.

9. The method of claim 1, wherein said hydrogel forming polymer has a number average molecular weight of at least about 250,000.

10. The method of claim 1, wherein said solid core particle is a hollow, mineral sphere.

11. The method of claim 1, wherein said co-suspending of said water resistant solid core particles occurs after a reaction exotherm has occurred.

12. The method of claim 1, wherein said surface active agent has an HLB factor of from about 2 to about 12.

13. The method of claim 12, wherein said surface active agent has an HLB value of from about 3 to about 7.

14. The method of claim 1, wherein said surface active agent is a fatty ester of a sugar optionally reacted with ethylene oxide.

15. The method of claim 1, wherein said water immiscible solvent is cyclohexane.

16. The method of claim 1, wherein said ethylenically unsaturated monomer is acrylic acid.

17. The method of claim 1, wherein said ethylenically unsaturated monomer is a partially neutralized acrylate-acrylic acid mixture.

18. The method of claim 1, wherein said initiator is potassium persulfate.

19. The method of claim 1, wherein said solid core particle is an inorganic mineral in particulate form.

20. The method of claim 1, wherein said solid core particle is silicon dioxide, titanium dioxide, magnesium oxide, antimony oxide, clay, talc, wollastonite, synthetic amorphous silica, or calcium carbonate.

21. The method of claim 1, wherein said solid core particle is sand.

22. The method of claim 1, wherein said solid core particle is cereal, wood flour, ground nut shells, cellulose, or gelatin in particulate form.

23. The method of claim 1, wherein said solid core particle is starch in particulate form.

24. The method of claim 1, wherein said solid core particle is silica and has a particle size of from about 50 microns to about 1000 microns.

25. The method of claim 24, wherein said particle size is from about 75 microns to about 500 microns.

26. The method of claim 1, wherein said hydrogel forming polymer has a thickness of from about 40 microns to about 150 microns.

27. The method of claim 1, wherein said water immiscible solvent is heptane.

28. The method of claim 1, wherein each absorbent particle comprises one water-resistant solid core particle with a size of from about 10 microns to about 1500 microns, substantially encapsulated by a composition consisting essentially of said hydrogel forming polymer, wherein said plurality of individual and discrete absorbent particles are in the substantial absence of absorbent particles containing none or more than one water resistant solid core particle.

* * * * *